United States Patent
Yamakawa et al.

(10) Patent No.: US 7,381,529 B2
(45) Date of Patent: Jun. 3, 2008

(54) METHODS AND COMPOSITIONS FOR DETECTING NUCLEIC ACIDS USING SCANNING PROBE MICROSCOPY AND NANOCODES

(75) Inventors: Mineo Yamakawa, Campbell, CA (US); Andrew Berlin, San Jose, CA (US)

(73) Assignee: Intel Corporation, Santa Clara, CA (US)

( * ) Notice: Subject to any disclaimer, the term of this patent is extended or adjusted under 35 U.S.C. 154(b) by 282 days.

(21) Appl. No.: 10/750,515

(22) Filed: Dec. 31, 2003

(65) Prior Publication Data

US 2005/0147981 A1 Jul. 7, 2005

(51) Int. Cl.
*C12Q 1/68* (2006.01)

(52) U.S. Cl. ......................................................... 435/6
(58) Field of Classification Search ..................... None
See application file for complete search history.

(56) References Cited

U.S. PATENT DOCUMENTS

| | | | | |
|---|---|---|---|---|
| 6,013,456 | A | 1/2000 | Akhavan-Tafti | 435/6 |
| 6,060,237 | A * | 5/2000 | Nygren et al. | 435/6 |
| 6,174,677 | B1 | 1/2001 | Vo-Dinh | 435/6 |
| 6,361,944 | B1 * | 3/2002 | Mirkin et al. | 435/6 |
| 6,514,767 | B1 | 2/2003 | Natan | 436/166 |
| 6,537,755 | B1 | 3/2003 | Drmanac | 435/6 |
| 2003/0148289 | A1 | 8/2003 | Sundararajan et al. | 435/6 |
| 2004/0058328 | A1 * | 3/2004 | Chan et al. | 435/6 |
| 2004/0126820 | A1 * | 7/2004 | Chan et al. | 435/7.4 |
| 2005/0147963 | A1 * | 7/2005 | Su et al. | 435/5 |
| 2005/0208554 | A1 * | 9/2005 | Chan et al. | 435/6 |

FOREIGN PATENT DOCUMENTS

| WO | WO 00/29617 | 5/2000 |
|---|---|---|
| WO | WO 01/25002 A1 | 4/2001 |
| WO | WO 2004/027095 A1 | 4/2004 |
| WO | WO 2004/038037 A2 | 5/2004 |

OTHER PUBLICATIONS

Nicewarner-Pena et al., "Submicrometer Metallic Barcodes", Science, Oct. 5, 2001, vol. 294, pp. 137-141.
Cao et al., "Nanoparticles with Raman Spectroscopic Fingerpoints for DNA and RNA Detection", Science, Aug. 30, 2002, vol. 297, pp. 1536-1540.
Doering, et al., "Spectroscopic Tags Using Dye-Embedded Nanoparticles and Surface—Enhanced Raman Scattering", *Analytical* Chemistry, :5-9.
Freitag, et al., "Local Electronic Properties of Single-Wall Nanotube Circuits Measured by Conducting Tip AFM", *Am. Phys. Soc.* 62(4):R2307-R2310, (Jul. 2000).
Han, et al., "Quantum-dot-tagged Microbeads for Multiplexed Optical Coding of Biomolecules", *Nat. Biotech.* 19:631-635 (Jul. 2001).
Mulvaney, et al., "Glass-Coated, Analyte-Tagged Nanoparticles: A New Tagging System Based on *Detection* with Surface-Enhanced Raman Scattering", *Am Chem Soc.* 19:4784-4790 (2003).

* cited by examiner

*Primary Examiner*—James Martinell
(74) *Attorney, Agent, or Firm*—Darby & Darby, P.C.

(57) ABSTRACT

A method for determining a nucleotide sequence of a nucleic acid is provided that includes contacting the nucleic acid with a series of labeled oligonucleotides for binding to the nucleic acid, wherein each labeled oligonucleotide includes a known nucleotide sequence and a molecular nanocode. The nanocode of an isolated labeled oligonucleotides that binds to the nucleic acid is then detected using SPM. Nanocodes of the present invention in certain aspects include detectable features beyond the arrangement of tags that encode information about the barcoded object, which assist in detecting the tags that encode information about the barcoded object. The detectable features include structures of a nanocode or associated with a nanocode, referred to herein as detectable feature tags, for error checking/error-correction, encryption, and data reduction/compression.

19 Claims, 5 Drawing Sheets

FIG. 4A  Example of barcode with molecular feature tags for reading frames and start/end markers
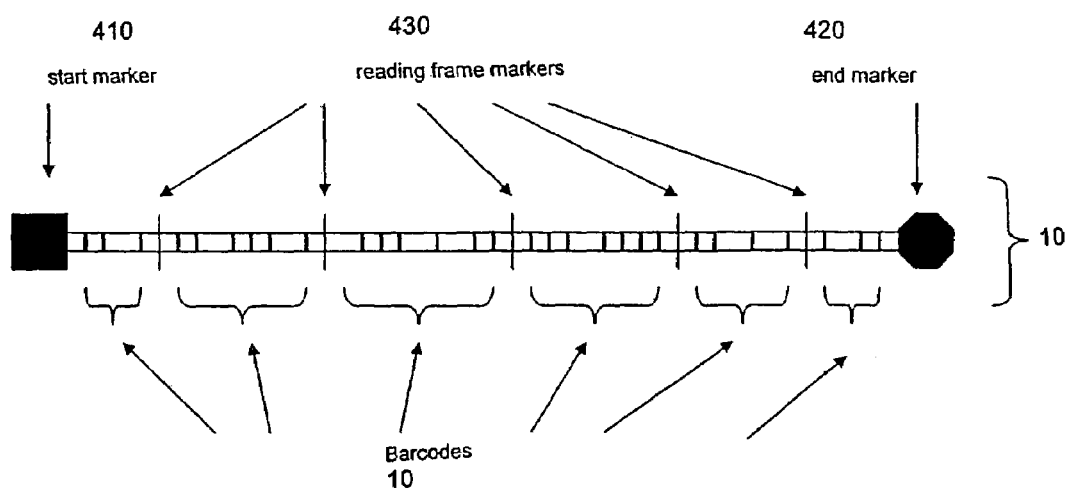
FIG. 4B  Example of barcode transformed into molecular feature tags for data compressions.
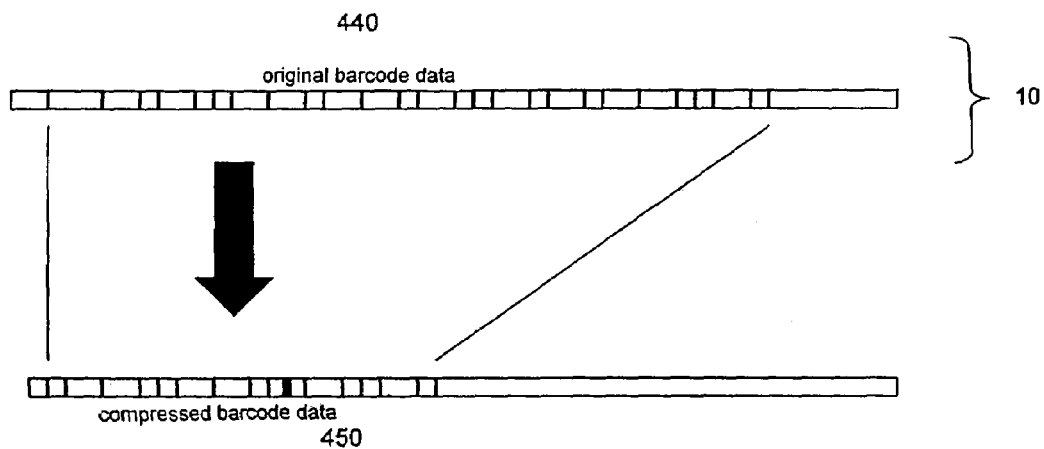
FIG. 4C  Example of barcode with molecular feature tags for checksum.
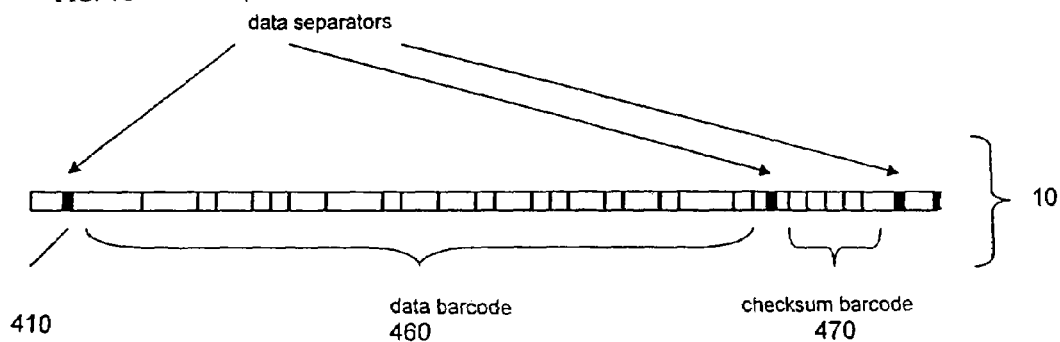

SEQUENCE LISTING

```
<160> NUMBER OF SEQ ID NOS: 1

<210> SEQ ID NO 1
<211> LENGTH: 30
<212> TYPE: PRT
<213> ORGANISM: Artificial sequence
<220> FEATURE:
<223> OTHER INFORMATION: Synthetic peptide

<400> SEQUENCE: 1

Ala Ala Met Ala Ala Lys Ala Met Ala Ala Met Ala Lys Ala Val Ala
1               5                   10                  15

Met Ala Ala Lys Ala Val Ala Ala Met Ala Lys Ala Ala Ala
            20                  25                  30
```

METHODS AND COMPOSITIONS FOR DETECTING NUCLEIC ACIDS USING SCANNING PROBE MICROSCOPY AND NANOCODES

BACKGROUND OF THE INVENTION

1. Field of the Invention

The invention relates generally to molecular analysis methods and more specifically to detecting molecules associated with nanocodes.

2. Background Information

The medical field, among others, is increasingly in need of techniques for identification and characterization of molecules. In particular, techniques for sequencing a DNA molecule have become more important due in part to recent medical advances utilizing genetics and gene therapy.

For a variety of reasons, it has become advantageous to know the sequence of particular DNA molecules. Methods currently exist to map the sequence of DNA, however existing methods are too cumbersome and slow to meet the current characterization and sequencing demands. One such current method includes Automated sequencing machines employing PCR amplification to make many copies of a molecule, followed by chemical (or radioactive) tagging, gel electrophoresis, and statistical computational methods to calculate the original sequence. This method is very time consuming, and not well suited for today's rapid sequencing demands. Additionally the statistical sequencing of PCR determination leaves a margin for error in characterization that is unacceptable.

For short sequences, a hybridization microarray based method is commonly used, employing biochips such as those marketed by Affymetrix, Inc. In these "DNA chips," multiple identical copies are made of detection molecules. The detection molecules consist of specific, short (<100 bases) sequences of DNA that are carefully synthesized such that their sequence is known. By detecting (typically optically) hybridization of unknown DNA to one of these detection molecules, the sequence of a short portion of the original DNA molecule can be inferred. A problem with the biochip method however, is that the detection molecules are too long to provide complete accuracy of detection.

A need exists for a device and method for sequencing polynucleotides that reduce the possibility of sequencing errors such as inconclusive readings and at faster speeds and at lower costs. Furthermore, a need exists for rapid, accurate and sensitive methods for detection, identification, and/or sequencing of biomolecules in general, such as nucleic acids and proteins.

BRIEF DESCRIPTION OF THE DRAWINGS

FIG. 1A provides steps of a specific example of a method disclosed herein. FIG. 1B provides a diagrammatic representation of a specific example of a method disclosed herein.

```
                                    (SEQ ID NO:1)
NH2-AAMAAKAMAAMAKAVAMAAKAVAAMAKAAA-CONH2.
```

FIGS. 4A to 4C illustrate embodiments for reading frame detectable features (FIG. 4A); data compression (FIG. 4B); and check sum (FIG. 4C).

Figure 5:
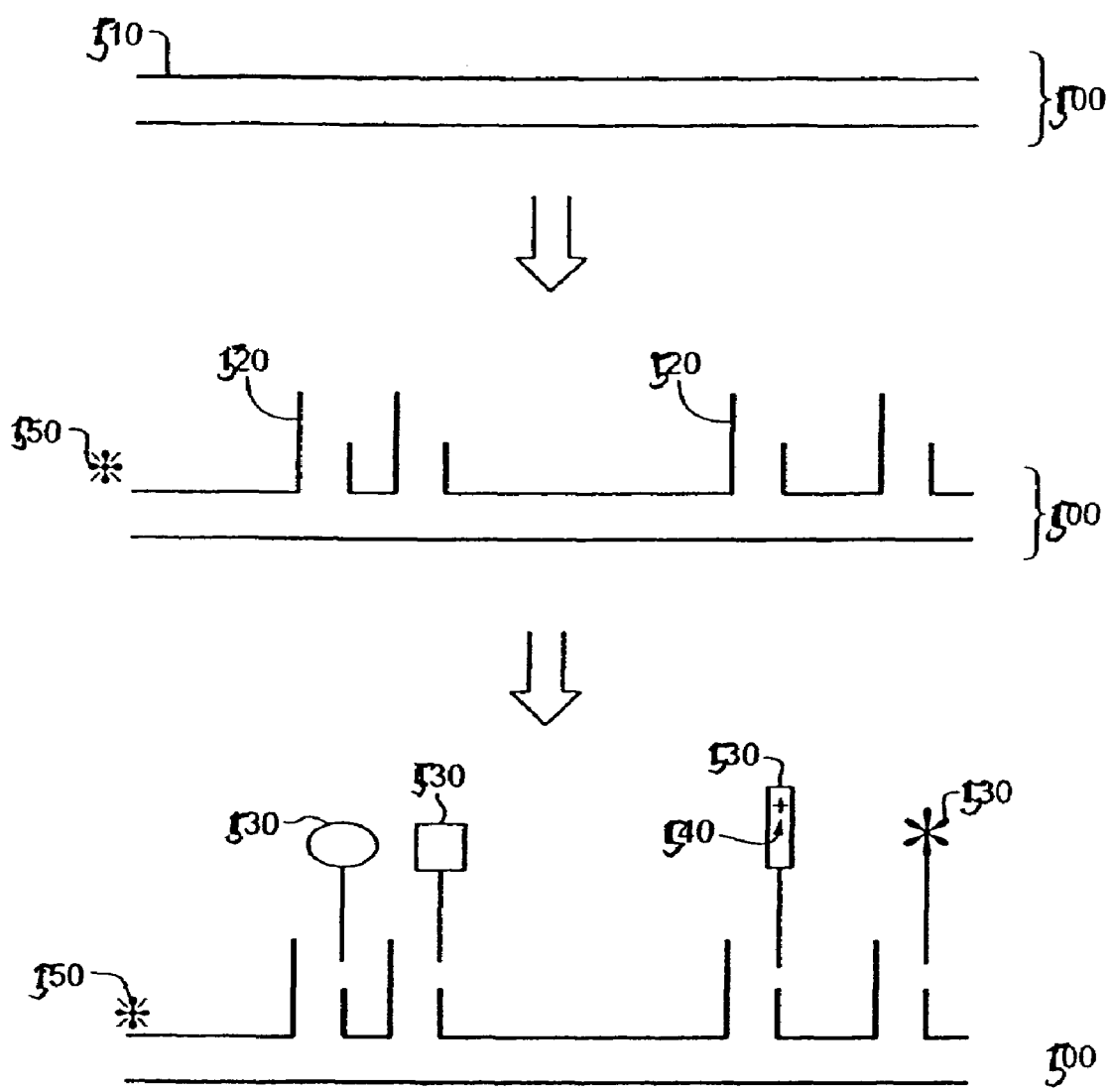

FIG. 5 illustrates an exemplary method for generating a barcode 500 with an organic backbone 510 modified with branches 520 and tags 530. The barcode 500 can include a probe moiety 550 to bind to a target. The tags 530 can be subject to additional modification, for example by binding to an antibody 540.

DETAILED DESCRIPTION OF THE INVENTION

The present invention in general relates to the discovery that information regarding a physical object, such as a nucleic acid, can be artificially encoded in biomolecular nanocodes and decoded at a single molecule level by a surface analysis method such as scanning probe microscopy. For example, several embodiments of the present invention are based on the discovery that scanning probe microscopy can be used to identify nanocodes in nucleotide hybridization reactions.

Accordingly, a method for detecting a target molecule, such as a target nucleic acid, is provided, that includes providing one or more coded probes such as coded oligonucleotide probes, and contacting the target molecule with the coded probes. Each probe includes a biomolecular core, such as an oligonucleotide, associated with at least one nanocode that includes a detectable non-encoding feature. Coded probes that bind to the target molecule are then identified using scanning probe microscopy (SPM) to detect the nanocode and the detectable feature of the coded probe.

In certain aspects, a library of coded probes that includes all possible sequences for a particular length of oligonucleotide, is contacted with the target molecule. The nanocode is selected from carbon nanotubes, fullerenes, submicrometer metallic barcodes, nanoparticles or quantum dots, for example. In certain aspects, the nucleic acid is attached to a surface.

The method can further include determining the sequence of oligonucleotides that bind to the nucleic acid. The target molecule can be a protein, a peptide, a glycoprotein, a lipoprotein, a nucleic acid, a polynucleotide, an oligonucleotide, a lipid, a glycolipid or a polysaccharide, for example.

A detectable non-encoding feature as used herein, is a feature that can be implemented using a detectable feature tag, also called a "non-encoding feature tag" or a "special feature tag." For example, the detectable non-encoding feature tag can be a start tag. In certain aspects, the detectable feature is a checksum barcode segment. In other aspects, the detectable feature includes a header segment and an encoding segment. In certain aspects, the method further includes transforming the molecular nanocode into a compressed nanocode. In other aspects, the method includes ligating together two probes that bind to adjacent regions on a target molecule. In these embodiments, the ligated probes can form reading frames, which can be marked with a reading frame marker.

In another aspect, a composition that includes at least one coded probe molecule attached to at least one nanocode that encodes a detectable non-encoding feature, is provided. The probe molecule is a specific binding pair member, for example, a nucleic acid, such as an oligonucleotide or a polynucleotide; a protein or peptide fragment thereof, such as a receptor or a transcription factor, an antibody or an antibody fragment, for example a genetically engineered antibody, a single chain antibody, or a humanized antibody; a lectin; a substrate; an inhibitor; an activator; a ligand; a hormone; a cytokine; a chemokine; and/or a pharmaceutical. In certain aspects, the probe molecule is an oligonucleotide.

In another embodiment, a system for nucleic acid sequencing, including a scanning probe microscope, a surface, and at least one coded probe attached to the surface, wherein the coded probe includes a nanocode that includes a detectable feature, is provided. In certain aspects, the coded probes are aligned on the surface by molecular combing.

In another embodiment, a method for determining a nucleotide sequence of a nucleic acid, such as a polynucleotide by contacting the nucleic acid with a series of labeled oligonucleotides for binding to the nucleic acid, wherein each labeled oligonucleotide includes a known nucleotide sequence and a molecular nanocode that includes a detectable non-encoding feature, is provided. Labeled oligonucleotides that bind to the nucleic acid are then isolated and the isolated labeled oligonucleotides are deposited on a scanning probe microscopy (SPM) substrate. The nanocode of the isolated labeled oligonucleotides and their associated detectable non-encoding feature is detected using SPM, for example. The nucleotide sequence of the isolated labeled oligonucleotides is then decoded based on one or more detected nanocode. Thus, a nucleotide sequence of the nucleic acid is determined. The nanocode can include a series of tags, in certain aspects of the invention.

Figure 1:
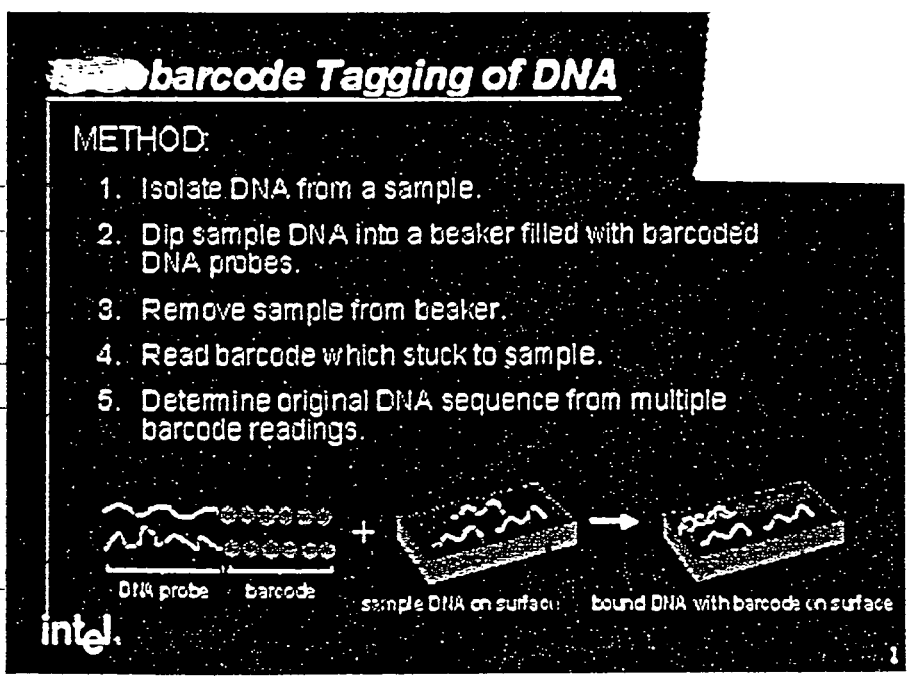
FIGS. 1A and 1B schematically illustrates one specific method of the invention for nanocode tagging of DNA for determining a nucleotide sequence of a nucleic acid molecule.

A specific example of this embodiment of the invention is illustrated in FIGS. 1A and 1B. In the method exemplified in FIGS. 1A and 1B, a nucleic acid such as DNA 60 is isolated from a sample 120. The sample DNA 60 is then introduced into a reaction vessel 130, such as a beaker, that includes a series of labeled oligonucleotides 80 (e.g. a coded library of oligonucleotide probes). The sample is then removed from the reaction vessel 140 and deposited on an SPM surface 50. Barcodes which bind to the sample are read 150. The method can be repeated such that a DNA sequence of the DNA sample is determined from multiple barcode readings 160.

In a related embodiment, a method for determining a nucleotide sequence of a target nucleic acid, such as a polynucleotide, in a biological sample, is provided that includes contacting the nucleic acid with a series of labeled oligonucleotides. The labeled nucleotides are for binding to the nucleic acid, wherein each labeled oligonucleotide includes a known nucleotide sequence and a molecular nanocode that includes a detectable non-encoding feature. Labeled oligonucleotides that bind to the nucleic acid are isolated. The isolated labeled oligonucleotides are deposited on a scanning probe microscopy substrate (SPM). Nanocodes on deposited labeled oligonucleotides, and their non-encoding detectable features, are then detected using SPM. The nucleotide sequence of the isolated labeled oligonucleotides is then determined based on the detected nanocodes, thereby determining a nucleotide sequence of the target nucleic acid in the biological sample.

The biological sample is, for example, urine, blood, plasma, serum, saliva, semen, stool, sputum, cerebral spinal fluid, tears, mucus, and the like. In certain aspects, the biological sample is from a mammalian subject, for example a human subject. The biological sample can be virtually any biological sample, particularly a sample that contains RNA or DNA from a subject. The biological sample can be a tissue sample which contains, for example, 1 to 10,000,000; 1000 to 10,000,000; or 1,000,000 to 10,000,000 somatic cells. The sample need not contain intact cells, as long as it contains sufficient RNA or DNA for the methods of the present invention, which in some aspects require only 1 molecule of RNA or DNA. According to aspects of the present invention wherein the biological sample is from a mammalian subject, the biological or tissue sample can be from any tissue. For example, the tissue can be obtained by surgery, biopsy, swab, stool, or other collection method.

In other aspects, the biological sample contains a pathogen, for example a virus or a bacterial pathogen. In certain aspects, the template nucleic acid is purified from the biological sample before it is contacted with a probe, however. The isolated template nucleic acid can be contacted with a reaction mixture without being amplified.

In other aspects, the biological sample contains a pathogen, for example a virus or a bacterial pathogen. In certain aspects, the template nucleic acid is purified from the biological sample before it is contacted with a probe, however. The isolated template nucleic acid can be contacted with a reaction mixture without being amplified.

In another embodiment, a method for determining a nucleotide occurrence at a target position of a nucleic acid such as a polynucleotide, is provided that includes contacting the nucleic acid with a series of labeled oligonucleotides for binding to the nucleic acid, wherein the labeled oligonucleotides include a known nucleotide sequence that binds to a nucleotide occurrence at the target position, and a molecular nanocode that typically includes a detectable non-encoding feature. Binding of the labeled oligonucleotides to the nucleic acid is detected using scanning probe microscopy (SPM) to detect the molecular nanocode and the detectable non-encoding feature of the bound labeled oligonucleotides. The identity of the molecular nanocode identifies the labeled oligonucleotide that binds the nucleotide occurrence at the target position of the nucleic acid.

In another embodiment, a method for determining a nucleotide occurrence for at least two target positions of a genome, is provided that includes contacting nucleic acids of the genome with a series of labeled oligonucleotides for binding to the nucleic acids, wherein the labeled oligonucleotides each include a known nucleotide sequence that binds to a nucleotide occurrence at one of the series of target positions, and a molecular nanocode that includes a detectable non-encoding feature. The series of labeled oligonucleotides typically includes oligonucleotides that specifically bind to one of at least the known nucleotide occurrences at the target positions. Binding of the labeled oligonucleotides to the nucleic acids is detected using scanning probe microscopy (SPM) to detect the molecular nanocode of the molecular nanocode of the detected oligonucleotides and the detectable non-encoding features. The identity of the molecular nanocode identifies the labeled oligonucleotide that binds the nucleotide occurrence at the target position of the nucleic acid. Thus, the nucleotide occurrence at the at least two target positions are determined. For example, the nucleotide occurrence at 2, 3, 4, 5, 10, 20, 25, 50, 100, 250, 500, 1000, 2500, 5000, or 10000 positions can be determined.

In certain aspects, the target position of a nucleic acid molecule is a site of a polymorphism such as a single nucleotide polymorphism position. Polymorphisms are allelic variants that occur in a population. A polymorphism can be a single nucleotide difference present at a locus, or can be an insertion or deletion of one or a few nucleotides. As such, a single nucleotide polymorphism (SNP) is characterized by the presence in a population of one or two, three or four nucleotide occurrences (i.e., adenosine, cytosine, guanosine or thymidine) at a particular locus in a genome such as the human genome. As indicated herein, methods of the invention in certain aspects, provide for the detection of a nucleotide occurrence at a SNP location or a detection of both genomic nucleotide occurrences at a SNP location, for a diploid organism such as a mammal.

In another embodiment, a nanocode that includes a detectable non-encoding feature, and is detectable by a single molecule level surface analysis method, is provided. Nanocodes of the present invention in certain aspects include detectable non-encoding features beyond the arrangement of nanocode structures that encode information about the barcoded object, which assist in detecting the tags that encode information about the barcoded object. The detectable non-encoding features include structures for error checking/error-correction, encryption, and data reduction/compression. These structures can be formed from a nanocode or associated with a nanocode, in which they are referred to herein as detectable non-encoding feature tags, feature tags or detectable feature tags. These detectable features can be used with known algorithms for non-barcode applications, to assist in data analysis of nanocoded data.

In another embodiment, a series of oligonucleotides that include a known nucleotide sequence portion, also referred to as a probe portion, for sequencing by hybridization, and a nanocode portion for subsequent reading and decoding of encoded information, is provided. The nanocode is a nanocode according to the present invention.

A nucleotide sequence determined using methods described herein can include a single nucleotide, such as a nucleotide occurrence at a single nucleotide polymorphism, or can include, for example, 2, 3, 4, 5, 10, 15, 20, 25, 50, 100, 200, 250, 500, 750, 1000, 2000, 2500, 5000, 10,000 etc., nucleotides.

Methods of the present invention in certain aspects provide the advantage that a smaller number of copies of a labeled oligonucleotide can be detected than with traditional labeling methods. For example, 100 copies or less, 50 copies or less, 25 copies or less, 10 copies or less, 5 copies or less, 4 copies or less, 3 copies or less, 2 copies or less, or a single copy of a labeled oligonucleotide can be detected using methods of the present invention.

As used herein, "about" means within ten percent of a value. For example, "about 100" would mean a value between 90 and 110.

"Nucleic acid" encompasses DNA, RNA (ribonucleic acid), single-stranded, double-stranded or triple stranded and any chemical modifications thereof. Virtually any modification of the nucleic acid is contemplated. A "nucleic acid" can be of almost any length, from oligonucleotides of 2 or more bases up to a full-length chromosomal DNA molecule. Nucleic acids include, but are not limited to, oligonucleotides and polynucleotides. A "polynucleotide" as used herein, is a nucleic acid that includes at least 25 nucleotides.

"Coded probe" refers to a probe molecule attached to one or more nanocodes. A probe molecule is any molecule that exhibits selective and/or specific binding to one or more target molecules. In various embodiments of the invention, each different probe molecule can be attached to a distinguishable nanocode, so that binding of a particular probe, from a population of different probe molecules, can be detected.

In certain embodiments of the invention, such as those directed to determining a nucleotide sequence of a nucleic acid, coded probes comprise oligonucleotides and/or nucleic acids that have been covalently or non-covalently attached to one or more nanocodes that identify the sequence of the oligonucleotide and/or nucleic acid. These coded probes are sometimes referred to herein as "coded oligonucleotides," "labeled oligonucleotides," or "coded oligonucleotide probes." In certain embodiments, each nucleotide within an oligonucleotide probe can be attached to a distinguishable nanocode, allowing the sequence of the coded probe to be identified from the sequence of nucleotides.

Certain embodiments are not limited as to the type of probe molecules that can be used. In these embodiments, any probe molecule known in the art, including but not limited to oligonucleotides, nucleic acids, antibodies, antibody fragments, binding proteins, receptor proteins, peptides, lectins, substrates, inhibitors, activators, ligands, hormones, cytokines, etc. can be used.

"Nanocode" refers to a composition that can be used to detect and/or identify a coded probe. In non-limiting examples discussed in more detail below, a nanocode includes one or more submicrometer metallic barcodes, carbon nanotubes, fullerenes or any other nanoscale moiety that can be detected and identified by scanning probe microscopy. Nanocodes are not limited to single moieties and in certain embodiments of the invention a nanocode can include, for example, two or more fullerenes attached to each other. Where the moieties are fullerenes, they can, for example, consist of a series of large and small fullerenes attached together in a specific order. The order of differently sized fullerenes in a nanocode can be detected by scanning probe microscopy and used, for example, to identify the sequence of an attached oligonucleotide probe.

As used herein, the term "specific binding pair member" refers to a molecule that specifically binds or selectively hybridizes to another member of a specific binding pair. Specific binding pair member include, for example, an oligonucleotide and a nucleic acid to which the oligonucleotide selectively hybridizes, or a protein and an antibody that binds to the protein.

A "target" or "analyte" molecule is any molecule that can bind to a coded probe, including but not limited to nucleic acids, proteins, lipids and polysaccharides. In some aspects of methods directed at encoding or decoding information about a physical object or methods for detecting a target molecule, binding of a coded probe to a target molecule can be used to detect the presence of the target molecule in a sample.

In certain aspects of the invention, nanocodes have detectable non-encoding features in addition to the structures or tags that encode information about the barcoded object, which assist in accurately detecting nanocodes. The detectable non-encoding features include structures of a nanocode or structures associated with a nanocode for error checking/error-correction, encryption, and data reduction/compression. The detectable non-encoding feature structures in certain aspects include start markers, end markers, and an arrangement of barcode units into reading frames that can be marked by reading frame tags. These detectable non-encoding features can be used with known algorithms for non-barcode applications, to assist in data analysis of nanocoded data. These detectable non-encoding features can be provided by the same type of tags that are used to encode information about the barcoded objects, or can be structurally different than tags used to encode information about the barcoded object, are discussed in further detail below.

Figure 2A:
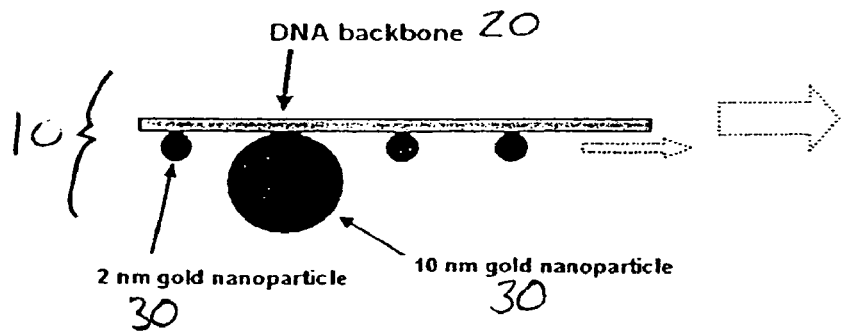
FIGS. 2A, 2B, and 2C illustrate barcode patterns for encoding individual nucleotides using gold nanoparticle 30 tags and a DNA backbone. The figure illustrates a 2 nm gold nanoparticle (small circle) and a 10 nm gold nanoparticle (large circle).
Figure 2B:
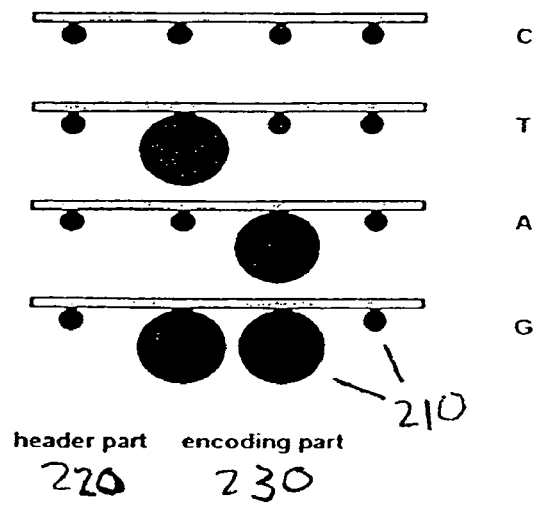

As an example of a detectable non-encoding feature, as illustrated in FIG. 2b, a nanocode 10 of the present invention in certain aspects, includes a header segment 210 and an encoding segment 220. The inclusion of both a header segment 220 and an encoding segment 230 assists in distinguishing detected nanocodes 10 from self-assembled structures. The size of nanoparticles and attachment locations (i.e., separation from adjacent nanoparticles) can distinguish the header segment from the encoding segment. For example, a library of coded oligonucleotide probes can each include an identical header segment 220 and distinct encoding segments 230. In certain aspects of the present invention, the nanocodes 10 are distinguishable using a single molecule level surface analysis method.

The nanocodes 10 of the present invention can be used in many different methods, for example methods used in biotechnology and/or health care. Such methods include, but not limited to, polynucleotide sequencing, immunoassays, single nucleotide polymorphism (SNP) detection, specific genotype detection, and ligand binding. The nanocodes are also useful for nanocode-based personal ID and security protocols.

In certain aspects of the invention, the molecular nanocode 10 encrypts information regarding the molecule that is associated with and identified by the nanocode 10. The encrypted information can be used for security purposes. Standard or specific encryption methods can be used. The encrypted nanocode can include a series of detectable non-encoding feature tags, for example that can be decrypted into encoding feature tags.

In certain aspects of the invention, the unique structural pattern or pattern of tags of a nanocode is transformed into compressed information, for example information regarding the nucleotide sequence of the labeled oligonucleotide. Compressed information allows a data size reduction. A nanocode that results from compression of a standard nanocode typically includes a series of detectable non-encoding feature tags that can be transformed into encoding tags. In certain aspects, the nanocode encodes at least 2 bits, 3 bits, 4 bits, 5 bits, or 10 bits of information. For example, a nanocode can identify an oligonucleotide of a specific length, as discussed further herein. If for example, each nanocode of a series of nanocodes are used to identify the nucleotide sequence of a series of oligonucleotides 5 nucleotides in length, the identity of a string of nanocodes that identify oligonucleotides that bind to adjacent regions of a target polynucleotide provide a 5:1 data reduction.

Any mathematical encryption/decryption and/or compression/decompression algorithm can be for these aspects related to encryption and compression examples. The nanocodes include a series of binary numbers (i.e., "0"s and "1"s) or other number system, where each element exactly corresponds to the element of the particular numbering system. For example, a "large circle," for example a relatively large gold particle, can represent "0" and "small circle" can represent "1". The resulting series of "0"s and "1"s are used as a binary number, which can be processed and manipulated mathematically as in information processing systems, including compression algorithms as used in the standard compression of computer files (i.e., binary sequences) such as "ZIP" files.

Figure 2C:
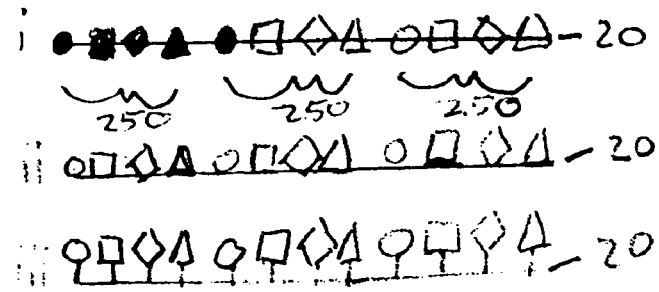

In certain aspects of the invention the detectable non-encoding feature tag is a start tag or end tag. The start tag and/or end tag can identify a header or footer region of the nanocode. For example, with reference to FIG. 2, each nanocode can include a gold particle of a certain size, such as a 2 nm gold nanoparticle (small circles in FIG. 2), as a header tag 210 or footer tag. If each nanocode in a series of nanocodes is the same length, or has the same number of tags, the header tag 210 or footer tag can be identified in order to confirm that the nanocode has the expected characteristics of the nanocode of the series of nanocodes. This provides a quality control check for detected nanocodes and to distinguish from self-assembled structures.

As shown in FIG. 2b, a series of barcodes can include the same header tag 210 in a header segment 220 and a series of tags in an encoding segment 230. In the example shown in FIGS. 2a and 2b, the size of nanoparticles and attachment locations (i.e., separation from adjacent nanoparticles) encode information such as nucleotide base sequence (header, C, T, A, G, . . . ). As described above, FIG. 2b, for example, illustrates encoding units, "C=0000", "T=0100", "A=0010", and "G=0110" where "0"s and "1"s are used to encode information, as disclosed above.

In certain aspects, a pattern of identifiable structures on a nanocode, such as a patterns of tags on a nanocode 10, is encoded as an "encoding unit" 250 based on a variety of different molecular properties. An encoding unit 250 is a pattern of identifiable structures or a series of tags that identifies a certain structure, typically a polymeric sequence of an object, such as a biomolecule, that is identified and associated with the nanocode 10 (i.e. a barcoded object). In certain aspects of the invention, a nanocode 10 includes a series of encoding units 250. The order and identity of the encoding units 250 identify the barcoded object. For example with reference to FIG. 2C, encoding units 250 can be a part of the main nanocode (i.e. nanocode backbone) 20, attached to the main nanocode without a linker (FIG. 2c(i)) or with a linker (FIG. 2c(ii)), or any other combination thereof. Furthermore, branched 2D and 3D structures can be used as encoding units.

The encoding units of nanocodes of certain aspects of the present invention are distinguishable based on a physical, chemical, optical, or electrical property. In one aspect, AFM is used to identify encoding units based on a topographic property, such as size of encoding unit, distance between encoding units, or atomic and molecular force of encoding units. AFM can also be used to identify encoding units based on a viscoelectric property of the encoding units such as in-phase and out-of-phase stiffness of encoding units or bonds between them. In another aspect, CFM or LFM are used to identify encoding units based on chemical force, depending on the chemical treatment of the probe tip and the sample. In another aspect, STM is used to identify encoding units based on a topographic property based on tunneling current, or an electrical property, based on conductivity or tunneling current. In yet another aspect, FE-SEM is used to identify encoding units of a nanocode based on a topographic property (i.e., electron reflection and dispersion). In yet another aspect, TEM is used to identify encoding units based on a topographic property (i.e. electron transmission). In yet another aspect, AES is used to identify encoding units based on a topographic property (i.e. Auger electron scattering). In yet another aspect, XPS is used to identify coding units based on chemical composition or chemical functionalization (i.e. primary and secondary photoelectron scattering of x-rays). In yet another aspect, TOF-SIMS is used to identify encoding units based on elemental or organic chemical composition. In yet another aspect, Raman spectroscopy is used to identify encoding units based on a chemical property such as molecular vibrations, crystal structures, or molecular orientation. In another aspect, Surface enhanced raman spectroscopy (SERS/SERRS) is used to identify the encoding units. In yet another exemplary aspect, fluorescence spectroscopy such as single molecule level fluorescence spectroscopy or fluorescence resonance transfer is used to identify encoding units based on a fluorescent property.

In addition to the encoding units 250 encoding information such as the identity of the encoded object, an encoding unit 250 or a series of encoding units 250 can be used as markers for the start and the end of barcode, specific reading frame indicators and data markers for such purposes as error-checking, error-corrections, data compressions, paragraphing, and encryptions, as discussed herein in further detail for the nanocode tags. The encoding units 250 can form encoding groups and/or can encode class definitions.

In certain aspects of the present invention, the nanocodes include molecular feature tags. Molecular feature tags are tags that are included on a molecular barcode that provide information that assists with identifying the barcode and the tags on the data encoding portion of the barcode. Typically, the feature tags are uniquely identifiable and measurable. The feature tags for example, can be different than a set of tags on a barcode that are used to identify an object associated with the barcode. As another example, the feature tags can be a different size but chemically similar or identical to data tags (i.e. tags in the data segment of a barcode). The molecular feature tags are useful for the methods described herein for encrypting information, identifying reading frames, identifying encoding units, error checking/error-correction, and data reduction/compression. As discussed for tags and encoding units, feature tags can be incorporated, embedded, attached to, or associated with a nanocode backbone. Feature tags can be used to indicate the start of the paragraph as described above or as periodic "redundant" reading frames, which can be used to re-synchronize or to identify any errors or any verifications of reading encoded information.

For example, as shown in FIG. 4A, molecular feature tags include start marker feature tags 410 or end marker feature tags 420 that label the beginning and end of a nanocode 10, respectively. These markers help in identifying individual nanocodes 10 and for identifying self-assembled barcodes that could cause misreading of properly assembled barcodes. The start marker is a type of header segment as discussed above.

Furthermore, as shown in FIG. 4A, "reading frames" can be incorporated into nanocodes using molecular feature tags. This allows synchronization of data capturing of the basic information unit for decoding similar to video frames, network/communication data packets, machine words (e.g., 64-bit data with 2-bit cyclic redundancy checksum), and data files with headers or start/end markers, for example. Since biomolecular nanocodes can exhibit variations in lengths, molecular bond properties, etc. between different data units/packets, the incorporations of reading frames marking each unit/packet within nanocodes significantly increases the speed and accuracy of data reading and synchronizations for scanning.

Reading frames can represent individual nanocodes 10 that are linked together, which can be separated by header parts 220, which in these embodiments form reading frame markers 430. In some aspects, reading frames markers 430 are non-barcode, non-molecular feature tags such as, for example, independent chemical markers, molecular structural components/elements.

As shown in FIG. 4B, the molecular feature tags can be used for data compression. In this aspect of the invention, original nanocode data 440 is compressed into a compressed barcode data 450 that includes a pattern of molecular feature tags that are fewer in number or spatially closer than the tags on the original nanocode.

The information in molecular feature tags can be retrieved using the same method used to identify the nanocode or the other tags on a nanocode. That is the molecular feature tags can be identified based on the same molecular properties used to detect the rest of the nanocode, even in examples where the feature tags are different molecules than other tags on the biomolecular nanocodes.

In certain aspects of the present invention, the barcodes include detectable features to provide error detection, error checking, and to accelerate barcode reading. For example, the nanocodes can include detectable feature tags that mark the start and end of a data segment 460 of a barcode (i.e., the portion of the barcode that provides information specific to the barcoded object). A nanocode of the present invention can also include a checksum barcode segment 470. The checksum barcode segment provides a quality control check to assure that an identified barcode is a member of a set or series of nanocodes. According to embodiments using a checksum segment, a data barcode is detected using a single molecule level surface analysis method such as SPM. In addition, the associated checksum barcode is detected. The data barcode and detected checksum barcode are then checked to assure that this combination of data barcode and checksum barcodes were associated together when a series of barcodes were made. This information provides an assurance that the barcode was not self-assembled.

"identifiable structures" and "molecular properties" are "encoding elements" such as "size/mass" (e.g., big vs. small) as measured by AFM and/or STM, or charge (e.g., strong charge vs. weak charge) as measured by STM. Once actual SPM properties are converted into encoding units (i.e., information), any standard information processing method can be used to further process the information, such as information processing methods known in bioinformatics for biotechnology applications. As an example, four binary digits can encode seven "separate" different encoding units: "0000", "0001"(="1000"), "0010" (="0100"), "1001", "1010" (="0101"), "1011" (="1101"), and "1110" (="0111"). If the exact start location of each encoding unit is identifiable, a series of encoding units can represent a series of bases/nucleic acids: CTAG="0000 0100 0010 0110". In practice, it is difficult to identify an exact location to start reading, and in the case of oligonucleotides, 2-digit encoding for four bases (e.g., C=00, T=10, A=01, G=11) can be used with "frames" places at the start and the end of encoding units. For example, if "0" is used as frames: CTAG=0000 0100 0010 0110. In this example, if two "0"s are in sequence, the next two digits are an encoding unit, representing C or T or A or G. Four "0"s in sequence, represents a frame start.

In addition to assisting in identifying the start of an encoded unit, reading frames can be used for error detections. For example, as a simplified example of error detection, two consecutive "0"s can be used to assure that a reading error at that location has not occurred. A more elaborated error correction scheme can be devised based on available algorithms. Additional sets of encoding units can be used to implement a standard checksum or error correcting codes as found in relevant, available algorithms. The checksum can be used to identify any non-encoded sequences, which can result from accidental spontaneous self-assembly or deletions occurred under unfavorable chemical/physical conditions/media. A set of reading units is described is a "paragraph."

In methods of the present invention related to determining a nucleotide sequence, a nucleic acid, such as a polynucleotide, to be at least partially sequenced, is contacted with a series of labeled oligonucleotides. Nucleic acid molecules to be detected, identified and/or sequenced can he prepared by any technique known in the art. In certain embodiments of the invention, the nucleic acids are naturally occurring DNA or RNA molecules. Virtually any naturally occurring nucleic acid can be detected, identified and/or sequenced by the disclosed methods including, without limit, chromosomal, mitochondrial and chloroplast DNA and ribosomal, transfer, heterogeneous nuclear and messenger RNA. In some embodiments, the nucleic acids to be analyzed can be present in crude homogenates or extracts of cells, tissues or organs. In other embodiments, the nucleic acids can be partially or fully purified before analysis. In alternative embodiments, the nucleic acid molecules to be analyzed can be prepared by chemical synthesis or by a wide variety of nucleic acid amplification, replication and/or synthetic methods known in the art.

Methods of the present invention analyze nucleic acids that in some aspects are isolated from a cell. Methods for purifying various forms of cellular nucleic acids are known. (See, e.g., Guide to Molecular Cloning Techniques, eds. Berger and Kimmel, Academic Press, New York, N.Y., 1987; Molecular Cloning: A Laboratory Manual, 2nd Ed., eds. Sambrook, Fritsch and Maniatis, Cold Spring Harbor Press, Cold Spring Harbor, N.Y., 1989). The methods disclosed in the cited references are exemplary only and any variation known in the art can be used. In cases where single stranded DNA (ssDNA) is to be analyzed, ssDNA can be prepared from double stranded DNA (dsDNA) by any known method. Such methods can involve heating dsDNA and allowing the strands to separate, or can alternatively involve preparation of ssDNA from dsDNA by known amplification or replication methods, such as cloning into M13. Any such known method can be used to prepare ssDNA or ssRNA.

Although certain embodiments of the invention concern analysis of naturally occurring nucleic acids, such as polynucleotides, virtually any type of nucleic acid could be used. For example, nucleic acids prepared by various amplification techniques, such as polymerase chain reaction (PCR™) amplification, could be analyzed. (See U.S. Pat. Nos. 4,683,195, 4,683,202 and 4,800,159.) Nucleic acids to be analyzed can alternatively be cloned in standard vectors, such as plasmids, cosmids, BACs (bacterial artificial chromosomes) or YACs (yeast artificial chromosomes). (See, e.g., Berger and Kimmel, 1987; Sambrook et al., 1989.) Nucleic acid inserts can be isolated from vector DNA, for example, by excision with appropriate restriction endonucleases, followed by agarose gel electrophoresis. Methods for isolation of nucleic acid inserts are known in the art. The disclosed methods are not limited as to the source of the nucleic acid to be analyzed and any type of nucleic acid, including prokaryotic, bacterial, viral, eukaryotic, mammalian and/or human can be analyzed within the scope of the claimed subject matter.

In various embodiments of the invention, multiple copies of a single nucleic acid can be analyzed by labeled oligonucleotide probe hybridization, as discussed below. Preparation of single nucleic acids and formation of multiple copies, for example by various amplification and/or replication methods, are known in the art. Alternatively, a single clone, such as a BAC, YAC, plasmid, virus, or other vector that contains a single nucleic acid insert can be isolated, grown up and the insert removed and purified for analysis. Methods for cloning and obtaining purified nucleic acid inserts are well known in the art.

It will be recognized that the scope of certain embodiments of the present invention is not limited to analysis of nucleic acids, but also concerns analysis of other types of biomolecules, including but not limited to proteins, lipids and polysaccharides. Methods for preparing and/or purifying various types of biomolecules are known in the art and any such method can be used.

In certain aspects, the series of labeled oligonucleotides are a series of oligonucleotides that can be used in a sequencing by hybridization reaction. In sequencing by hybridization one or more tagged barcodes including oligonucleotide probes of known sequence are hybridized to a target nucleic acid sequence. Binding of the tagged barcode to the target indicates the presence of a complementary sequence in the target strand. Multiple labeled barcodes can be hybridized simultaneously to the target molecule and detected simultaneously. In alternative embodiments, bound probes can be identified attached to individual target molecules, or alternatively multiple copies of a specific target molecule can be allowed to bind simultaneously to overlapping sets of probe sequences. Individual molecules can be scanned, for example, using known molecular combing techniques coupled to a detection mode. (See, e.g., Bensimon et al., Phys. Rev. Lett. 74:4754-57, 1995; Michalet et al., Science 277:1518-23, 1997; U.S. Pat. Nos. 5,002,867, 5,840,862; 6,054,327; 6,225,055; 6,248,537; 6,265,153; 6,303,296 and 6,344,319.)

Sequencing by hybridization methods provided herein can include one or more capture oligonucleotide probes that bind to the target nucleic acid. The capture oligonucleotide probes can be spotted on a biochip. The identity of a bound probe and a location of a capture probe on a biochip can both be used to determine nucleotide sequence information regarding the target nucleic acid.

In certain aspects, a sequencing by hybridization method includes an optional ligation reaction. The ligation reaction typically involves ligation of a capture oligonucleotide probe to a coded oligonucleotide probe that binds to an adjacent region of a target nucleic acid. After adjacent oligonucleotides are ligated, oligonucleotides that are not immobilized to the substrate are removed, for example by elevating the temperature or changing the pH of a reaction to denature nucleic acids. Oligonucleotides that are not immobilized to the substrate either directly or indirectly can be washed away and the immobilized coded oligonucleotide probes and optionally capture probes, can be detected. The ligation and wash steps increase the specificity of the reaction.

Adjacent labeled oligonucleotide probes can be ligated together using known methods (see, e.g., U.S. Pat. No. 6,013,456). Primer independent ligation can be accomplished using oligonucleotides of at least 6 to 8 bases in length (Kaczorowski and Szybalski, *Gene* 179:189-193, 1996; Kotler et al., *Proc. Natl. Acad. Sci. USA* 90:4241-45, 1993). Methods of ligating oligonucleotide probes that are hybridized to a nucleic acid template are known in the art (U.S. Pat. No. 6,013,456). Enzymatic ligation of adjacent oligonucleotide probes can utilize a DNA ligase, such as T4, T7 or Taq ligase or *E. coli* DNA ligase. Methods of enzymatic ligation are known (e.g., Sambrook et al., 1989).

In various embodiments of the invention, hybridization of a target nucleic acid to a coded oligonucleotide library can be performed under stringent conditions that only allow hybridization between fully complementary nucleic acid sequences. Low stringency hybridization is generally performed at 0.15 M to 0.9 M NaCl at a temperature range of 20° C. to 50° C. High stringency hybridization is generally performed at 0.02 M to 0.15 M NaCl at a temperature range of 50° C. to 70° C. It is understood that the temperature and/or ionic strength of an appropriate stringency are determined in part by the length of an oligonucleotide probe, the base content of the target sequences, and the presence of formamide, tetramethylammonium chloride or other solvents in the hybridization mixture. The ranges mentioned above are exemplary and the appropriate stringency for a particular hybridization reaction is often determined empirically by comparison to positive and/or negative controls. The person of ordinary skill in the art is able to routinely adjust hybridization conditions to allow for only stringent hybridization between exactly complementary nucleic acid sequences to occur.

It is unlikely that a given target nucleic acid will hybridize to contiguous probe sequences that completely cover the target sequence. Rather, multiple copies of a target can be hybridized to pools of coded oligonucleotides and partial sequence data collected from each. The partial sequences can be compiled into a complete target nucleic acid sequence using publicly available shotgun sequence compilation programs. Partial sequences can also be compiled from populations of a target molecule that are allowed to bind simultaneously to a library of barcode probes, for example in a solution phase.

The series of oligonucleotides themselves form another embodiment of the present invention. The series of oligonucleotides are also referred to herein as a "coded oligonucleotide library." The series of oligonucleotides are typically hybridization probes that include a known nucleotide sequence portion, also referred to as a probe portion, for sequencing by hybridization, and a nanocode portion for subsequent reading and decoding of encoded information.

The length of the nucleotide sequence portion and the associated nanocode portion can be varied based on the particular requirements for subsequence analysis. In certain aspects the series includes oligonucleotides with nucleotide sequences that correspond to every possible permutation less than or equal to the length of the oligonucleotides. The length of the oligonucleotide portion and associated barcode portion can be varied based on the particular requirements for detection. For example, the oligonucleotide portion of the labeled oligonucleotide, in certain aspects is equal to or less than 250 nucleotides, 200 nucleotides, 100 nucleotides, 50 nucleotides, 25 nucleotides, 20 nucleotides, 15 nucleotides, 10 nucleotides, 9 nucleotides, 8 nucleotides, 7 nucleotides, 6 nucleotides, 5 nucleotides, 4 nucleotides, or 3 nucleotides in length. For example, but not intended to be limiting, the oligonucleotide is 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 200, or 250 nucleotides in length.

The series of labeled oligonucleotides in certain aspects, includes at least 10, 20, 30, 40, 50, 100, 200, 250, 500, 1000, oligonucleotides. For example, the series can include substantially all, or all of the possible nucleotide sequence combination for oligonucleotides of an identical length, as is known for at least some sequencing by hybridization reactions (See e.g., U.S. Pat. No. 5,002,867). Substantially all of the possible nucleotide sequence combinations for a given length, includes enough of the possible nucleotide sequences to allow decoding of a sequence using sequencing by hybridization.

In certain aspects, all of the oligonucleotides in the series of labeled oligonucleotides that have an identical probe portion includes the same unique nanocode. In other aspects, more than one oligonucleotide with a different probe portion is attached to an identical nanocode so that a group of particular sequence patterns can be identified faster by scanning and decoding.

In certain embodiments of the invention, coded probes, such as labeled oligonucleotides, can be detected while still attached to a target molecule. Given the relatively weak strength of the binding interaction between short oligonucleotide probes and target nucleic acids, such methods can be more appropriate where, for example, coded probes have been covalently attached to the target molecule using cross-linking reagents.

In various embodiments of the invention, oligonucleotide type coded probes can be DNA, RNA, or any analog thereof, such as peptide nucleic acid (PNA), which can be used to identify a specific complementary sequence in a nucleic acid. In certain embodiments of the invention one or more coded probe libraries can be prepared for hybridization to one or more nucleic acid molecules. For example, a set of coded probes containing all 4096 or about 2000 non-complementary 6-mers, or all 16,384 or about 8,000 non-complementary 7-mers can be used. If non-complementary subsets of oligonucleotide coded probes are to be used, a plurality of hybridizations and sequence analyses can be carried out and the results of the analyses merged into a single data set by computational methods. For example, if a library comprising only non-complementary 6-mers were used for hybridization and sequence analysis, a second hybridization and analysis using the same target nucleic acid molecule hybridized to those coded probe sequences excluded from the first library can be performed.

In certain aspects of the invention, the coded probe libraries include a random nucleic acid sequence in the middle of the coded probe attached to constant nucleic acid sequences at one or both ends. For example, a subset of 12-mer coded probes can be used that consists of a complete set of random 8-mer sequences attached to constant 2-mers at each end. These coded probe libraries can be subdivided according to their constant portions and hybridized separately to a nucleic acid, followed by analysis using the combined data of each different coded probe library to determine the nucleic acid sequence. The skilled artisan will realize that the number of sublibraries required is a function of the number of constant bases that are attached to the random sequences. An alternative embodiment can use multiple hybridizations and analyses with a single coded probe library containing a specific constant portion attached to random oligonucleotide sequences. For any given site on a nucleic acid, it is possible that multiple coded oligonucleotide probes of different, but overlapping sequence could bind to that site in a slightly offset manner. Thus, using multiple hybridizations and analyses with a single library, a complete sequence of the nucleic acid could be obtained by compiling the overlapping, offset coded probe sequences.

In aspects of the invention involving oligonucleotide libraries, oligonucleotides can be prepared by any known method, such as by synthesis on an Applied Biosystems 381A DNA synthesizer (Foster City, Calif.) or similar instruments. Alternatively, oligonucleotides can be purchased from a variety of vendors (e.g., Proligo, Boulder, Colo.; Midland Certified Reagents, Midland, Tex.). In embodiments where oligonucleotides are chemically synthesized, the nanocodes can be covalently attached to one or more of the nucleotide precursors used for synthesis. Alternatively, the nanocode can be attached after the oligonucleotide probe has been synthesized. In other alternatives, the nanocode(s) can be attached concurrently with oligonucleotide synthesis.

In certain aspects of the invention, coded probes include peptide nucleic acids (PNAs). PNAs are a polyamide type of DNA analog with monomeric units for adenine, guanine, thymine, and cytosine. PNAs are commercially available from companies such as PE Biosystems (Foster City, Calif.). Alternatively, PNA synthesis can be performed with 9-fluoroenylmethoxycarbonyl (Fmoc) monomer activation and coupling using 0-(7-azabenzotriazol-1-yl)-1,1,3,3-tetramethyluronium hexafluorophosphate (HATU) in the presence of a tertiary amine, N,N-diisopropylethylamine (DIEA). PNAs can be purified by reverse phase high performance liquid chromatography (RP-HPLC) and verified by matrix assisted laser desorption ionization—time of flight (MALDI-TOF) mass spectrometry analysis.

In certain embodiments a library of probe molecules is provided, with each different probe attached to a distinguishable nanocode. The probes are not restricted to oligonucleotide probes. Within a given library, as is the case for the coded oligonucleotide libraries, it is possible that there can be more than one copy of a specific probe molecule. In this case, each copy of the same probe can be attached to an identical nanocode. The types of probes and nanocodes used for these aspects are not limiting and any known type of probe molecule, including but not limited to oligonucleotides, nucleic acids, antibodies, antibody fragments, binding proteins, receptor proteins, peptides, lectins, substrates, inhibitors, activators, ligands, hormones, cytokines, etc. can be used. Further, any type of distinguishable nanocode can be used.

In certain aspects of the present invention, the series of labeled oligonucleotides includes a pattern of tags that are arranged to provide error checking, as discussed in further detail herein. In certain aspects of the invention, the unique pattern of tags form compressed information regarding the nucleotide sequence of the labeled oligonucleotide. In certain aspects of the invention the series of labeled oligonucleotides include a common start tag to provide quality control, as discussed in further detail herein. In certain aspects of the invention, the series of oligonucleotides include a pattern of tags that encrypt information regarding the nucleotide sequence of the labeled oligonucleotide.

After the polynucleotide is contacted with the series of labeled oligonucleotides, labeled oligonucleotides that bind (i.e. hybridize) to the polynucleotide are isolated. This typically involves separating hybridized from non-hybridized oligonucleotides using known techniques. The separation can be carried out using physical, chemical, electrical, or any other methods known in the art. For example, unhybridized labeled oligonucleotides (i.e. coded oligonucleotide probes) can be separated from coded probes hybridized to the target molecule using known methods, such as high performance liquid chromatography (HPLC), gel permeation chromatography, gel electrophoresis, ultrafiltration and/or hydroxylapatite chromatography.

The isolated labeled oligonucleotides, or tags that have been stripped from the isolated labeled oligonucleotides, are then deposited on the surface of a scanning probe microscopy (SPM) substrate. That is, full probe molecules can be deposited on the surface, or probes that have hybridized can be isolated/separated, and the nanocode parts stripped away for separate reading and decoding in the absence of the probe molecule. For example, the polynucleotide can be separated from the isolated labeled oligonucleotides before detection of the nanocodes associated with the isolated labeled oligonucleotides.

For example, nanocodes are captured in a micro-scale (or smaller scale) analytical system in a dry or wet state for SPM analysis, or for a single molecule level surface analysis in embodiments involving such analysis. If necessary, an appropriate immobilization and dispersion technique can be used to improve the SPM analysis. For example, in SPM methods a substrate surface treatment such as thiol-gold, polylysine, silanization/AP-mica, as well as Mg2+ and/or Ni2+ (See e.g., Proc. Natl. Acad. Sci. USA 94:496-501 (1997); Biochemistry 36:461 (1997); Analytical Sci. 17:583 (2001); Biophysical Journal 77:568 (1999); and Chem. Rev. 96:1533 (1996)) can be used to uniformly disperse and immobilize a labeled polynucleotide. The appropriate dispersion allows for single molecule level analysis to be performed for reading and decoding information.

In various embodiments of the invention, nanocodes coded probes and/or target molecules bound to coded probes can be attached to a surface and aligned for analysis. In some embodiments, coded probes can be aligned on a surface and the incorporated nanocodes detected as discussed herein. In alternative embodiments, nanocodes can be detached from the probe molecules aligned on a surface and detected. In certain embodiments, the order of coded probes bound to an individual target molecule can be retained and detected, for example, by scanning probe microscopy. In other embodiments, multiple copies of a target molecule can be present in a sample and the identity and/or sequence of the target molecule can be determined by assembling all of the sequences of coded probes binding to the multiple copies into an overlapping target molecule sequence. Methods for assembling, for example, overlapping partial nucleic acid or protein sequences into a contiguous sequence are known in the art. In various embodiments, nanocodes can be detected while they are attached to probe molecules, or can alternatively be detached from the probe molecules before detection.

Methods and apparatus for attachment to surfaces and alignment of molecules, such as nucleic acids, oligonucleotide probes and/or nanocodes are known in the art (See, e.g., Bensimon et al., Phys. Rev. Lett. 74:4754-57, 1995; Michalet et aL, Science 277:1518-23, 1997; U.S. Pat. Nos. 5,840,862; 6,054,327; 6,225,055; 6,248,537; 6,265,153; 6,303,296 and 6,344,319; see also U.S. patent application Ser. No. 10/251,152, filed Sep. 20, 2002, entitled "Controlled Alignment of Nanocodes Encoding; Specific Information for Scanning Probe Microscopy (SPM)"). Nanocodes, coded probes and/or target molecules can be attached to a surface and aligned using physical forces inherent in an air-water meniscus or other types of interfaces. This technique is generally known as molecular combing. Nanocodes, coded probes and/or target molecules dissolved in an aqueous medium can be attached at either one or both ends to a surface, such as a silanized glass slide, a biotinylated surface, a gold-coated surface or any other surface known in the art capable of binding such molecules. The surface can be slowly withdrawn from the aqueous medium. Polar or charged target molecules, nanocodes, and/or coded probe molecules will preferentially partition into the hydrophilic (aqueous) medium. Thus, removal of the surface from the aqueous medium results in stretching of the bound target molecules, nanocodes and/or coded probes, parallel to the direction of movement of the meniscus. There is a direct correlation between the measured length of the stretched molecule and its actual size, with 1 μm of stretched length corresponding to about 2,000 bases of nucleic acid sequence (Herrick et al., Proc. Natl. Acad. Sci. USA 97:222-227, 2000).

Once the surface has been entirely removed from the aqueous medium, the attached nanocodes and/or coded probes are aligned in a parallel fashion that can be more easily and accurately analyzed. In certain embodiments of the invention where both ends of a coded probe are attached to the surface, the aligned coded probes will be arranged in a U-shaped conformation that is also more easily analyzed. The technique is not limited by the size of the target molecules, nanocodes and/or coded probes to be aligned, and can work on nucleic acids as long as whole chromosomes (e.g., Michalet et al., 1997; Herrick et al., 2000). At appropriate rates of movement of the meniscus the shear forces generated are relatively low, resulting in aligned DNA fragments of several hundred kilobases or longer (Michalet et al., 1997).

Molecular combing is inhibited by strong nonspecific adsorption of molecules to the treated surface (Bensimon et al., 1995). Thus, in various embodiments of the invention, the surface is treated so that only one or more ends of a target molecule or coded probe will bind to the surface. Methods for binding nucleic acids and other types of coded probes to surfaces are well known in the art and are summarized herein. In a non-limiting example, target molecules, nanocodes or coded probes can be covalently modified with biotin residues at one or both ends of the molecule. Upon exposure to an avidin or streptavidin coated surface only the biotinylated ends will bind to the surface. Nonspecific adsorption to a surface can be decreased by the use of surfaces that are hydrophobic in nature, such as silanized surfaces.

The embodiments of the invention are not limited by the type of surface that is used. Non-limiting examples of surfaces include glass, functionalized glass, ceramic, plastic, polystyrene, polypropylene, polyethylene, polycarbonate, PTFE (polytetrafluoroethylene), PVP (polyvinylpyrrolidone), germanium, silicon, quartz, gallium arsenide, gold, silver, nylon, nitrocellulose or any other material known in the art that is capable of having target molecules, nanocodes and/or coded probes attached to the surface. Attachment can be either by covalent or noncovalent interaction. Although in certain embodiments of the invention the surface is in the form of a glass slide or cover slip, the shape of the surface is not limiting and the surface can be in any shape. In some aspects of the invention, the surface is planar.

It is contemplated that any known method of alignment can be used within the scope of the claimed subject matter. In certain embodiments of the invention, alignment occurs when target molecules, nanocodes or coded probes dissolved in an aqueous medium are drawn through a moving meniscus. The mechanism by which the meniscus is moved is not important and can be accomplished, for example, by immersing a surface in buffer solution and slowly withdrawing it from the solution. Alternatively, a surface can be immersed in a solution and the level of the meniscus can be slowly lowered by evaporation or by removal of liquid.

In another alternative aspect of the invention, a drop of solution can be placed between a cover slip and a surface, such as a glass slide. The surface can be slowly pulled away from the cover slip. Because the solution adheres to the cover slip, this results in the formation of an air-water interface at the edge where the cover slip contacts the surface. Moving this interface aligns the target molecules, nanocodes and/or coded probes on the surface. Another alternative method for aligning nanocodes and/or coded probes, involves use of free-flow electrophoresis either in place of or during molecular combing.

After the labeled oligonucleotides or stripped tags are deposited, the barcodes that are deposited are identified by detecting the pattern of tags using SPM. This is accomplished by scanning the surface using SPM. This allows information retrieval and decoding. The nucleotide sequence of the isolated labeled oligonucleotides is then decoded based on the identified deposited nanocode. The data, often in a form of scanned images, are analyzed and processed through standard or customized/specialized image processing or digital signal processing techniques and software such as software provided by SPM manufacturers or any other image/signal processing software available. The information read (and decoded) can be stored in a separate data storage system or transferred to computer systems for further data processing.

Methods for using the identification of hybridizing oligonucleotides to decode sequence information is known in the art. For example, the cited references related to sequencing by hybridization included herein provides detailed methods for decoding polynucleotide sequence information based on a sequencing by hybridization result. Data collected from multiple nanocode readings are used to determine the polynucleotide sequence. Bioinformatics companies and government agencies provide necessary tools, services, and other associated tools for data processing to determine DNA sequences. For example, there are a significant number of UNIX software packages available for Sun SPARCstation and Linux clusters as both public domain and commercial software. Examples are: "SCORE" by ESTSC (Energy Science & Technology Software Center), and "Software for DNA sequencing by hybridization" *Bioinformatics* 113:205 (1997), or computer applications in *Biosciences* 13:205 (1997).

In certain aspects of methods of the invention for determining the nucleotide sequence of the polynucleotide, scanning probe microscopy (SPM) is used to detect nanocodes. The SPM detection is performed either in a dry state or in a wet state. For example, dried barcodes can be read by AFM or STM. Wet barcodes (i.e., non-dried) can be read by fluidic AFM or fluidic STM. That is, the detection can be performed by analyzing and processing scanned SPM images. The information read and decoded can be stored in a separate data storage system or transferred to computer systems for further data processing.

Examples of scanning probe microscopy techniques include scanning tunneling microscopy (STM), atomic force microscopy (AFM), scanning capacitance microscopy, and scanning optical microscopy, as well as other methods as discussed herein.

One of the advantages of the method of the present invention for determining a polynucleotide sequence, is that the use of SPM with molecular nano-scale barcodes can be performed with much lower concentrations of the polynucleotide to be sequenced than traditional sequencing methods. Thus, requirements for polynucleotide amplification are minimized, or in some cases eliminated. Thus, fewer copies of the labeled oligonucleotide are required for detection than for other detection techniques. In some aspects, 10,000 or less, 5,000 or less, 2500 or less, 1000 or less, 500 or less, 250 or less, 100 or less, 50 or less, 25 or less, 10 or less, 5 or less, 4 or less, 3 or less, 2 or less, or 1 copy of the labeled oligonucleotide is detected. Typically, there is one pattern of tags for every labeled oligonucleotide.

In certain embodiments, more than one biomolecular nanocode are detected on one polynucleotide molecule. For example, during a sequencing by hybridization reaction, more than one labeled oligonucleotide can bind to the polynucleotide to be sequenced. The polynucleotide with bound labeled oligonucleotides can be deposited on an SPM substrate and the bound labeled oligonucleotides can be detected. In certain aspects of the invention, the order of more than one biomolecule nanocodes is determined and used to decode nucleotide sequence information regarding the target polynucleotide (i.e. the polynucleotide to be at least partially sequenced). The detection of the order of more than one nanocode increases the speed at which the polynucleotide sequence is decoded.

In certain aspects, the method of determining a nucleotide sequence further includes an optional ligation reaction, wherein the biomolecular barcodes are detected on one polynucleotide molecule. The ligation reaction involves oligonucleotides that bind to adjacent regions on a polynucleotide that can be detected in their adjacent arrangement by SPM. In other words, in this aspect of the invention, a linear series of coded oligonucleotide probes are ligated together. Each coded oligonucleotide probe in the ligated molecule can be attached to a distinguishable nanocode to allow its identification. Since the sequence of coded oligonucleotide probes in a ligated molecule can also be determined, the sequence of the entire ligated molecule can be identified.

Adjacent coded oligonucleotide probes can be ligated together using known methods (see, e.g., U.S. Pat. No. 6,013,456). Oligonucleotide sequences of as short as 6 to 8 bases can be efficiently hybridized to target nucleic acids (U.S. Pat. No. 6,013,456). Primer independent ligation can be accomplished using oligonucleotides of at least 6 to 8 bases in length (Kaczorowski and Szybalski, Gene 179:189-193, 1996; Kotler et al., Proc. Natl. Acad. Sci. USA 90:4241-45, 1993). Methods of ligating oligonucleotide coded probes that are hybridized to a nucleic acid template are known in the art (U.S. Pat. No. 6,013,456). Enzymatic ligation of adjacent oligonucleotide coded probes can utilize a DNA ligase, such as T4, T7 or Taq ligase or *E. coli* DNA ligase. Methods of enzymatic ligation are known (e.g., Sambrook et al., 1989).

The methods of the present invention utilize nanocodes, which themselves form an embodiment of the present invention. The nanocodes can be virtually any length, but are typically 0.5 nm-1 µm in all dimensions, and in certain examples are 1 nm-500 nm in all dimensions. For example, the nanocode is typically between 1 nm and 500 nm in length. Furthermore, the nanocodes are typically soluble in aqueous and organic phases (amphiphilic). In certain aspects, the barcodes self-assemble, are viscoelastic, form networks, and/or are conductive.

The molecular barcodes of the present invention are typically molecular nanocodes. Molecular nanocodes in certain aspects include a backbone and a series of tags that identify an object associated with the nanocode. Each nanocode uniquely identifies a specific biomolecule to which it is associated, such as a nucleotide. The barcodes can be distinguishable based on the structure of the nanocode backbone itself or of the spatial relationship and/or identities of the tags (i.e. pattern of tags) on the nanocode. As discussed in more detail below, tags include, but are not limited to, conducting, luminescent, fluorescent, chemiluminescent, bioluminescent, Raman active (e.g., SERS or SERRS active), and phosphorescent moieties, quantum dots, nanoparticles, metal nanoparticles, gold nanoparticles, silver nanoparticles, chromogens, antibodies, antibody fragments, genetically engineered antibodies, enzymes, magnetic particles and spin label compounds. (U.S. Pat. Nos. 3,817,837;

3,850,752; 3,939,350; 3,996,345; 4,277,437; 4,275,149; and 4,366,241.) In one aspect, the tags include an oligonucleotide or a polynucleotide.

The nanocode in certain aspects, as discussed in more detail below, is a nucleotide, a peptide, a fullerene, a metal nanoparticle, an organometalic compound, a fluorescent molecule, a high-energy phosphate compound, and/or a carbon nanotube. In certain aspects, the nanocode is other than a carbon nanotube.

The nanocodes are distinguishable based on one or more physical, chemical, optical, and/or electrical properties. In embodiments for using the nanocodes to encode information about a physical object, the nanocodes are typically detected using a single molecule level surface analysis technique, as discussed in more detail herein. In embodiments related to polynucleotide sequencing and SNP detection, the nanocodes are typically detected using surface probe microscopy, as discussed in more detail herein.

Nanocodes in certain aspects of the present invention are biomolecular nanocodes. Biomolecular nanocodes include a biomolecule as at least a portion of the nanocode. Biomolecular barcodes can include chemical compounds. For example, the biomolecules can include a polypeptide, a polynucleotide, and/or a polysaccharide.

Certain aspects and embodiments of the present invention include or utilize a series of nanocodes, such as biomolecular nanocodes. For example, in certain embodiments of the present invention, a series of physical objects can be encoded using a series of molecular nanocodes. A series of nanocodes includes at least two, for example, 3, 4, 5, 10, 15, 20, 25, 50, 100, 250, 500, 1000, 2500, 5000, 10,000, 25,000, or 100,000 nanocodes that are structurally related. In certain aspects of the invention, for example those directed at methods that employ sequencing by hybridization, the series of nanocodes are associated with a series of oligonucleotides, wherein each nucleotide with a unique sequence is identified by a unique nanocode. In certain aspects of the invention, the molecular nanocodes of a series include an identical macromolecular scaffold. For example, all of the nanocodes can include a peptide backbone that is decorated with tags, such as C(60) tags, as illustrated in the Examples herein. In another embodiment, as shown in FIG. 2, the series of nanocodes 10 can include a nucleic acid backbone 20 wherein a nanotag 30, or a series of detectably distinct nanotags 30 that are bound at known distances from each other along the backbone 10 of a nanocode. The tags can be, for example, metal spheres, such as gold spheres. For example, the gold nanoparticles can be between about 1 mn and 1000 nm in length.

In certain aspects of the invention the nanocode is modified before detection. In one example, the nanocode that is detected is a modified nanotube, for example, as disclosed in U.S. patent application Publication (2003/0148289).

Several embodiments of the present invention are based on the discovery that single molecule level surface analysis methods can be used to identify biomolecular nanocodes to encode information regarding a physical objects. Accordingly, in another embodiment, a method for encoding and decoding information regarding a physical object, is provided that includes providing a nanocode that in certain aspects includes a biomolecular scaffold and a pattern of tags. The biomolecular nanocode is associated with a physical object such that information regarding the physical object is encoded on the biomolecular nanocode. The nanocode is detected using a single molecule level surface analysis method. The information encoded by the biomolecule nanocode is then decoded based on the detection of the tags, thereby encoding and decoding information regarding the physical object.

In certain aspects of this embodiment, nanocodes include detectable features that provide for data encryption, compression, or reading frames, as discussed herein. Furthermore, the detectable features in certain aspects, provide a header segment and an encoding segment to a nanocode, and can mark the start or end of a barcode. In certain aspects, the detectable features are provided by detectable feature tags that are associated with the nanocodes.

Nanocodes used in the methods of this aspect of the invention are typically biomolecular nanocodes, as disclosed in detail herein. The methods of this aspect of the invention can be used in various biotechnology and healthcare applications. The barcodes of the invention can be used for many different methods, for example methods used in biotechnology and/or health care including DNA sequencing, immunoassays, single nucleotide polymorphism (SNP) detection, specific genotype detection, and ligand binding. The nanocodes are also useful for nanocode based personal ID and security protocols.

According to this embodiment the present invention, nanocodes are read using a single molecule level surface analysis technique. Single molecule level surface analysis techniques, techniques which detect a single molecule or a small number of molecules, include, for example, Scanning Tunneling Microscopy (STM), scanning optical microscopy, scanning capacitance microscopy, atomic force microscopy (AFM), chemical force microscopy (CFM), lateral force microscopy (LFM), field emission scanning electron microscopy (FE-SEM), transmission electron microscopy (TEM), scanning TEM, Auger electron spectroscopy (AES), X-ray photoelectron spectroscopy (XPS), time-of-flight secondary ion mass spectrometry (TOF-SIMS), vibrational spectroscopy, Raman spectroscopy, or fluorescence spectroscopy.

Typically, the barcodes are distinguishable based on a physical, chemical, optical, or electrical property, as discussed herein. In one aspect, the single molecule level surface analysis techniques is AFM and the barcodes are distinguishable based on a topographic property or viscoelectric property. In another aspect the single molecule level surface analysis techniques is CFM or LFM and the barcodes are distinguishable based on chemical force. In another aspect, the single molecule level surface analysis techniques is STM and the barcodes are distinguishable based on a topographic property or an electrical property. In yet another aspect, the single molecule level surface analysis techniques is FE-SEM and the barcodes are distinguishable based on a topographic property. In yet another aspect, the single molecule level surface analysis techniques is TEM and the barcodes are distinguishable based on a topographic property. In yet another aspect, the single molecule level surface analysis techniques is AES and the barcodes are distinguishable based on a topographic property. In yet another aspect, the single molecule level surface analysis techniques is XPS and the barcodes are distinguishable based on chemical composition or chemical functionalization. In yet another aspect, the single molecule level surface analysis techniques is TOF-SIMS and the barcodes are distinguishable based on chemical composition. In yet another aspect, the single molecule level surface analysis techniques is Raman spectroscopy and the barcodes are distinguishable based on a chemical property. In still another aspect, the single molecule level surface analysis techniques is fluorescence spectroscopy and the barcodes are distinguishable based on a fluorescent property.

In certain aspects of the methods of the present invention, the tags on the nanocode include raman tags. Furthermore, these tags can include composite organic-inorganic nanoparticles (referred to herein as COIN nanoparticles or "COINs"). COINs are Raman-active probe constructs that include a core and a surface, wherein the core includes a metallic colloid including a first metal and a Raman-active organic compound. The COINs can further comprise a second metal different from the first metal, wherein the second metal fotms a layer overlying the surface of the nanoparticle. The COINs can further comprise an organic layer overlying the metal layer, which organic layer comprises the probe. Suitable probes for attachment to the surface of the SERS-active nanoparticles for this embodiment include, without limitation, antibodies, antigens, polynucleotides, oligonucleotides, receptors, ligands, and the like. However, for these embodiments, COINs are typically attached to an oligoriucleotide probe.

The metal for achieving a suitable SERS signal is inherent in the COIN, and a wide variety of Raman-active organic compounds can be incorporated into the particle. Indeed, a large number of unique Raman signatures can be created y employing nanoparticles containing Raman-active organic compounds of different structures, mixtures, and ratios. Thus, the methods described herein employing COINs are useful for the simultaneous determination of nucleotide sequence information from more than one, and typically more than 10 target nucleic acids. In addition, since many COINs can be incorporated into a single nanoparticle, the SERS signal from a single COIN particle is strong relative to SERS signals obtained from Raman-active materials that do not contain the nanoparticles described herein. This situation results in increased sensitivity compared to Raman-techniques that do not utilize COINs.

COINs are readily prepared for use in the invention methods using standard metal colloid chemistry. The preparation of COINs also takes advantage of the ability of metals to adsorb organic compounds. Indeed, since Raman-active organic compounds are adsorbed onto the metal during formation of the metallic colloids, many Raman-active organic compounds can be incorporated into the COIN without requiring special attachment chemistry.

In general, the COINs used in the invention methods are prepared as follows. An aqueous solution is prepared containing suitable metal cations, a reducing agent, and at least one suitable Raman-active organic compound. The components of the solution are then subject to conditions that reduce the metallic cations to form neutral, colloidal metal particles. Since the formation of the metallic colloids occurs in the presence of a suitable Raman-active organic compound, the Raman-active organic compound is readily adsorbed onto the metal during colloid formation. This simple type of COIN is referred to as type I COIN. Type I COINs can typically be isolated by membrane filtration. In addition, COINs of different sizes can be enriched by centrifugation.

In alternative embodiments, the COINs can include a second metal different from the first metal, wherein the second metal forms a layer overlying the surface of the nanoparticle. To prepare this type of SERS-active nanoparticle, type I COINs are placed in an aqueous solution containing suitable second metal cations and a reducing agent. The components of the solution are then subject to conditions that reduce the second metallic cations so as to form a metallic layer overlying the surface of the nanoparticle. In certain embodiments, the second metal layer includes metals, such as, for example, silver, gold, platinum, aluminum, and the like. This type of COIN is referred to as type II COINs. Type II COINs can be isolated and or enriched in the same manner as type I COINs. Typically, type I and type II COINs are substantially spherical and range in size from about 20 nm to 60 nm. The size of the nanoparticle is selected to be very small with respect to the wavelength of light used to irradiate the COINs during detection.

Typically, organic compounds, such as oligonucleotides, are attached to a layer of a second metal in type II COINs by covalently attaching the organic compounds to the surface of the metal layer Covalent attachment of an organic layer to the metallic layer can be achieved in a variety ways well known to those skilled in the art, such as for example, through thiol-metal bonds. In alternative embodiments, the organic molecules attached to the metal layer can be crosslinked to form a molecular network.

The COIN(s) used in the invention methods can include cores containing magnetic materials, such as, for example, iron oxides, and the like. Magnetic COINs can be handled without centrifugation using commonly available magnetic particle handling systems. Indeed, magnetism can be used as a mechanism for separating biological targets attached to magnetic COIN particles tagged with particular biological probes.

As indicated herein, one advantage of the methods of the present invention is that they allow detection of fewer molecules, such as for example, physical objects in this embodiment of the invention. For example, a method of this aspect of the invention can detect 10000 or less, 1000 or less, 500 or less, 250 or less, 100 or less, 50 or less, 25 or less, 20 or less, 15 or less, 10 or less, 9 or less, 8 or less, 7 or less, 6 or less, 5 or less, 4 or less, 3 or less, 2 or less, or 1 nanocode and/or physical object.

In certain aspects of this embodiment, the biomolecular nanocodes are deposited on a scanning probe microscopy (SPM) substrate before being detected by SPM, as discussed above for embodiments related to polynucleotide sequencing. In certain aspects of the invention, the encoding and decoding is performed for a series of physical objects using a series of molecular nanocodes. In certain aspects, the biomolecular nanocode is separated from the physical object before the pattern of tags is detected.

The physical object can be virtually any physical object. In certain aspects of the present invention, the physical object is a polynucleotide, a polypeptide, or a polysaccharide. In aspects where the physical object is a polynucleotide, the biomolecular nanocode, for example, provides information regarding the nucleotide sequence of the polynucleotide. In aspects where the physical object is a polypeptide, the biomolecular nanocode, for example, provides information regarding the amino acid sequence of the polypeptide. In aspects where the physical object is a polysaccharide, the biomolecular nanocode, for example, provides information regarding the identity of the monosaccharide subunits of the polysaccharide.

In certain embodiments, the physical object that is associated with a barcode is an aptamer. Aptamers are oligonucleotides derived by an in vitro evolutionary process called SELEX (e.g., Brody and Gold, *Molecular Biotechnology* 74:5-13, 2000). The SELEX process involves repetitive cycles of exposing potential aptamers (nucleic acid ligands) to a target, allowing binding to occur, separating bound from free nucleic acid ligands, amplifying the bound ligands and repeating the binding process. After a number of cycles, aptamers exhibiting high affinity and specificity against virtually any type of biological target can be prepared. Because of their small size, relative stability and ease of preparation, aptamers can be well suited for use as probes. Since aptamers are comprised of oligonucleotides, they can easily be incorporated into nucleic acid type barcodes. Methods for production of aptamers are well known (e.g., U.S. Pat. Nos. U.S. Pat. Nos. 5,270,163; 5,567,588; 5,670, 637; 5,696,249; 5,843,653). Alternatively, a variety of aptamers against specific targets can be obtained from commercial sources (e.g, Somalogic, Boulder, Colo.). Aptamers are relatively small molecules on the order of 7 to 50 kDa.

In certain embodiments, the physical object that is associated with a barcode is an antibody. Methods of production of antibodies are also well known in the art (e.g., Harlow and Lane, *Antibodies: A Laboratory Manual*, Cold Spring Harbor Laboratory, Cold Spring Harbor, N.Y., 1988.) Monoclonal antibodies suitable for use as probes can also be obtained from a number of commercial sources. Such commercial antibodies are available against a wide variety of targets. Antibody probes can be conjugated to barcodes using standard chemistries, as discussed below.

The disclosed methods and compositions are not limiting as to the type of probe used, and any type of probe moiety known in the art can be attached to barcodes and used in the disclosed methods. Such probes can include, but are not limited to, antibody fragments, affibodies, chimeric antibodies, single-chain antibodies, ligands, binding proteins, receptors, inhibitors, substrates.

In a related embodiment, a method for identifying a target molecule is provided that includes contacting the target molecule with a labeled probe or a series of labeled probes, wherein the target molecule and the probe are a specific binding pair, and wherein each labeled probe includes a molecular nanocode that includes a pattern of tags. Binding of a labeled probe to the target molecule is detected using scanning probe microscopy (SPM) to detect the molecular nanocode of the detected probe. The identity of the molecular nanocode identifies the labeled probe that binds the target molecule. In certain aspects of this embodiments, the molecular nanocodes include detectable feature tags or other structures to provide encryption, error checking, headers, start tags, compressed data, etc. as discussed herein. Furthermore, the series of labeled probes can be a library of coded oligonucleotide probes, as discussed herein.

In certain aspects the target molecule is a protein. In these aspects, the probe can be, for example, an antibody. In another aspect, the probe is a ligand. In this aspect, the target molecule is, for example, a polynucleotide. In another aspect, the target molecule is a polynucleotide. In this aspect, the probe is, for example, a polynucleotide that binds the target molecule.

The method can be used to detect one or more different target molecules. For example, the method can be used to detect 2 or more (i.e. a population of target molecules), 3 or more, 4 or more, 5 or more, 10 or more, 25 or more, 50 or more, 100 or more, 250 or more, 500 or more, or 1000 or more different target molecules.

The molecular signatures in single nanocode molecules can be implemented/encoded based on any physical, chemical, optical, electrical, and other molecular characteristics, which are captured and analyzed by the analysis methods discussed herein to retrieve information from the nanocodes.

As discussed herein, each coded probe typically incorporates at least one covalently or non-covalently attached nanocode. The nanocodes can be used to detect and/or identify individual coded probes. In certain embodiments of the invention each coded probe can have two or more attached nanocodes, the combination of which is unique to a particular coded probe. Combinations of nanocodes can be used to expand the number of distinguishable nanocodes available for specifically identifying a coded probe in a library. In other embodiments of the invention, the coded probes can each have a single unique nanocode attached. The only requirement is that the signal detected from each coded probe must be capable of distinguishably identifying that coded probe from different coded probes.

In certain embodiments of the invention, a nanocode can be incorporated into a precursor prior to the synthesis of a coded probe. For oligonucleotide-based coded probes, internal amino-modifications for covalent attachment at adenine (A) and guanine (G) positions are contemplated. Internal attachment can also be performed at a thymine (T) position using a commercially available phosphoramidite. In some embodiments library segments with a propylamine linker at the A and G positions can be used to attach nanocodes to coded probes. The introduction of an internal aminoalkyl tail allows post-synthetic attachment of the nanocode. Linkers can be purchased from vendors such as Synthetic Genetics (San Diego, Calif.). In one embodiment of the invention, automatic coupling using the appropriate phosphoramidite derivative of the nanocode is also contemplated. Such nanocodes can be coupled to the 5'-terminus during oligonucleotide synthesis.

In general, nanocodes will be covalently attached to the probe in such a manner as to minimize steric hindrance with the nanocodes, in order to facilitate coded probe binding to a target molecule, such as hybridization to a nucleic acid. Linkers can be used that provide a degree of flexibility to the coded probe. Homo-or hetero-bifunctional linkers are available from various commercial sources.

The point of attachment to an oligonucleotide base will vary with the base. While attachment at any position is possible, in certain embodiments attachment occurs at positions not involved in hydrogen bonding to the complementary base. Thus, for example, attachment can be to the 5 or 6 positions of pyrimidines such as uridine, cytosine and thymine. For purines such as adenine and guanine, the linkage is can be via the 8 position. The claimed methods and compositions are not limited to any particular type of probe molecule, such as oligonucleotides. Methods for attachment of nanocodes to other types of probes, such as peptide, protein and/or antibody probes, are known in the art.

The embodiments of the invention are not limiting as to the type of nanocode that can be used. It is contemplated that any type of nanocode known in the art can be used. Non-limiting examples include carbon nanotubes, fullerenes and submicrometer metallic barcodes, as discussed in more detail herein.

In certain aspects, the nanocode is a metallic barcode. Examples of submicrometer metallic barcodes of potential use as nanocodes are known in the art (e.g., Nicewarner-Pena et al., Science 294:137-141, 2001). Nicewarner-Pena et al. (2001) disclose methods of preparing multimetal microrods encoded with submicrometer stripes, comprised of different types of metal. This system allows for the production of a very large number of distinguishable nanocodes—up to 4160 using two types of metal and as many as $8 \times 10^5$ with three different types of metal. Such nanocodes can be incorporated into coded probes and read by SPM technology. Methods of attaching metal particles, such as gold or silver, to oligonucleotide and other types of probe molecules are known in the art (e.g., U.S. Pat. No. 5,472, 881).

Another exemplary type of nanocode useful in the disclosed methods is a carbon nanotube, such as a single-walled carbon nanotubes (SWNTs). Nanotubes can be made in a variety of shapes and sizes that can be distinguished by SPM methods. (See, e.g. Freitag et al., Phys. Rev. B 62: R2307-R2310, 2000; Clauss et al., Europhys. Lett. 47:601-607, 1999; Clauss et al., Phys. Rev. B. 58: R4266-4269, 1998; Odom et al., Ann. N.Y. Acad. Sci. 960:203-215, 2002). Odom et al. (2002) disclose an STM (scanning tunneling microscope) technique that is capable of detecting discrete peaks in the tunneling spectra of SWNTs of 10 nm or less in size. Such peaks can represent van Hove singularities in the density of electronic states (DOS) of the carbon nanotubes.

The electronic properties of carbon nanotubes are modulated by the length and diameter of the tube. The sensitivity of the electronic wavefunction to length is illustrated by an estimate for the energy level splitting of a tube of length L.

$$\Delta E = h v F / 2 L \qquad (\text{Eq. 1})$$

Where h is Planck's constant and vF is the Fermi velocity ($8.1 \times 10^5$ m/sec) (Venema et al., "Imaging Electron Wave Functions of Carbon Nanotubes," Los Alamos Physics Preprints:cond-mat/9811317, 23 Nov. 1996.) The difference between electron energy levels is inversely proportional to the length of the nanotube, with finer splitting observed for longer tubes.

The optical properties of carbon nanotubes are also a function of tube diameter. The relationship between fundamental energy gap (highest occupied molecular orbital—lowest unoccupied molecular orbital) and tube diameter can be modeled by the following function.

$$E_{gap} = 2 y_o a_{cc} / d \qquad (\text{Eq. 2})$$

Where $y_0$ is the carbon-carbon tight bonding overlap energy (2.7 2 0.1 eV), $a_{cc}$ is the nearest neighbor carbon-carbon distance (0.142 nm) and d is the tube diameter (Jeroen et al., Nature 391:59-62, 1998).

For certain embodiments of the invention, nanotubes to be used as nanocodes can have tube lengths of about 10 to 200 nm and a diameter of about 1.2 to 1.4 nm. The length or diameter of the nanotubes to be used as nanocodes is not limited and nanotubes of virtually any length or diameter are contemplated.

It is contemplated that nanotubes can be prepared by known methods or obtained from commercial sources, for example, CarboLex (Lexington, Ky.), NanoLab (Watertown, Mass.), Materials and Electrochemical Research (Tucson, Ariz.) or Carbon Nano Technologies Inc. (Houston, Tex.). Some processing of either synthesized or purchased nanotubes can be appropriate before use. Processing can include purification of nanotubes from other contaminants, separation of nanotubes of mixed diameter and/or length into nanotubes of discrete diameter and length, removal of nanotube end caps and/or covalent modification to facilitate attachment of the nanotube to a probe to form a coded probe.

In certain embodiments of the invention, carbon nanotubes of varying length and/or diameter can be produced by a variety of techniques known in the art, including but not limited to carbon-arc discharge, chemical vapor deposition via catalytic pyrolysis of hydrocarbons, plasma assisted chemical vapor deposition, laser ablation of a catalytic metal-containing graphite target, or condensed-phase electrolysis. (See, e.g., U.S. Pat. Nos. 6,258,401, 6,283,812 and 6,297,592.) In some embodiments, nanotubes can be size sorted by mass spectrometry (See, Parker et al., J. Am. Chem. Soc. 113:7499-7503, 1991). Alternatively, nanotubes can be sorted using an AFM (atomic force microscope) or STM (scanning tunneling microscope) to precisely measure the geometry of individual nanotubes before incorporating them into coded probes. Other methods of size fractionation known in the art, such as gas chromatography, time of flight mass spectrometry, ultrafiltration or equivalent techniques are contemplated. Once sorted, the carbon nanotubes can be derivatized and covalently attached to oligonucleotide probes of known sequence or any other type of probe.

The minimum incremental change in tube length possible for a carbon nanotube is the length of the carbon-carbon bond, or about 0.142 nm. With a range of tube lengths of 200 nm, this would allow for about 1400 discrete nanocodes. However, the method is not limited to a single nanotube per coded probe. In alternative embodiments, multiple nanotubes of different length and diameter can be attached to a single coded probe. Using combinations of nanotubes of different length, the number of possible distinguishable nanocodes increases exponentially. In some embodiments, a single nanotube can be attached to a single probe molecule for simplicity of analysis.

Other embodiments of the invention concern methods of producing carbon nanotubes of defined length and diameter. In a non-limiting exemplary embodiment, a chip can contain a layer of SiC of preselected thickness, overlaying a layer composed, for example, of silicon or silicon doped with catalysts (e.g. metal atoms such as nickel). Using standard chip processing methods, such as photolithography and etching or laser ablation, the SiC layer can be divided into SiC deposits of any length, width, thickness and shape. Subsequently the chip can be heated under a vacuum, for example at about 10-7 Torr at about 1400° C., or alternatively from about to Torr, to $10^{-3}$ to $10^{-12}$ Torr, $10^{-4}$ to $10^{-10}$ Torr, or $10^{-5}$ to $10^{-9}$ Torr, and from 1200 to 2200° C. or 1400 to 2000° C. Under these conditions, SiC crystals spontaneously decompose and lose silicon atoms (U.S. Pat. No. 6,303,094). The remaining carbon atoms spontaneously assemble into carbon nanotubes. The size and shape of the SiC deposits can be precisely controlled to produce carbon nanotubes of any length and diameter.

The exemplary embodiments of the invention discussed above are not limiting and any method of producing carbon nanotubes of selected length and diameter can be used (e.g., U.S. Pat. Nos. 6,258,401; 6,283,812 and 6,297,592). In some embodiments, nanotube length can be adjusted by using a laser beam, electron beam, ion beam or gas plasma beam to trim the ends. Alternatively, the ends of the nanotubes could be brought into contact with a hot blade in an oxygen-containing atmosphere to oxidatively remove the ends of the tubes. A block containing the nanotubes could also be sectioned or polished to truncate she nanotubes.

In certain embodiments of the invention, carbon nanotubes can be derivatized with reactive groups to facilitate attachment to probe molecules. In a non-limiting example, nanotubes can be derivatized to contain carboxylic acid groups (U.S. Pat. No. 6,187,823). Carboxylate derivatized nanotubes can be attached to probe molecules by standard chemistries, for example by carbodiimide mediated formation of an amide linkage with a primary or secondary amine group located on the probe. The methods of derivatization and cross-linking are not limiting and any reactive group or cross-linking methods known in the art can be used.

In alternative embodiments of the invention, fullerenes can be used to as nanocodes. Methods of producing fullerenes are well known (e.g., U.S. Pat. No. 6,358,375). Fullerenes can be derivatized and attached to probe molecules by methods similar to those disclosed above for carbon nanotubes. Fullerene-containing coded probes can be identified by SPM technologies, similar to those disclosed above for nanotubes.

In certain embodiments of the invention, fullerenes can be attached to individual nucleotides in an oligonucleotide coded probe. In such case, only two different types of distinguishable fullerenes are required, as there are only four types of nucleotide found in an oligonucleotide and two types of fullerenes can be combined in four different combinations (e.g., AA, BB, AB and BA). Where individual nucleotides are attached to nanocodes, it can be appropriate to use known linking groups between the nucleotide and the fullerene to avoid steric hindrance with hybridization to target nucleic acids.

The skilled artisan will realize that nanocodes of use in the disclosed methods are not limited to the embodiments disclosed herein, but can include any other type of known nanocode that can be attached to a probe and detected. Other non-limiting examples of nanocodes of potential use include quantum dots (e.g., Schoenfeld, et al., Proc. 7th Int. Conf. on Modulated Semiconductor Structures, Madrid, pp. 605-608, 1995; Zhao, et al., 1st Int. Conf. on Low Dimensional Structures and Devices, Singapore, pp. 467-471, 1995). Quantum dots and other types of nanocodes can be synthesized by known methods and/or obtained from commercial sources (e.g., Quantum Dot Corp., Hayward, Calif.). Other nanocodes of potential use include nanoparticles, available, for example, from Nanoprobes Inc. (Yaphank, N.Y.) and Polysciences, Inc. (Warrington, Pa.).

Another aspect of a nanocode useful in methods of the invention, as illustrated in FIG. 5, includes a barcode backbones 510 that can be formed from polymer chains comprising organic structures, including any combination of nucleic acid, peptide, polysaccharide, and/or chemically derived polymer sequences. In certain embodiments, the backbone 510 can comprise single or double-stranded nucleic acids. In some embodiments, the backbone can be attached to a probe moiety 550, such as an oligonucleotide, antibody or aptamer. The backbone 510 can be modified with one or more branch structures 520 to create additional morphological diversity and tag attachment sites. Branch structures 520 can be formed using techniques well known in the art. For example, where the barcode 500 comprises a double-stranded nucleic acid, branch structures 520 can be formed by synthesis of oligonucleotides and hybridization to a single-stranded template nucleic acid. The oligonucleotides can be designed so that part of the sequence (e.g., the 5' end) is complementary to the template and part (e.g., the 3' end) is not. Thus, the barcode 500 will contain segments of double-stranded sequence and short segments of single-stranded branch structures 520. As disclosed in FIG. 5, tags 530 can be added to the barcode, for example by hybridization of labeled 530 oligonucleotides that are complementary in sequence to the single-stranded portions of the branch structures 520.

Oligonucleotide mimetics can be used to generate the organic backbone 510. Both the sugar and the internucleoside linkage, i.e., the backbone, of the nucleotide units can be replaced with novel groups. The probes 550 can be used to hybridize with an appropriate nucleic acid target compound. One example of an oligomeric compound or an oligonucleotide mimetic that has been shown to have excellent hybridization properties is referred to as a peptide nucleic acid (PNA). In PNA compounds, the sugar-backbone of an oligonucleotide is replaced with an amide containing backbone, for example an aminoethylglycine backbone. In this example, the nucleobases are retained and bound directly or indirectly to an aza nitrogen atom of the amide portion of the backbone. Several United States patents that disclose the preparation of PNA compounds include, for example, U.S. Pat. Nos. 5,539,082; 5,714,331; and 5,719,262. In addition, PNA compounds are disclosed in Nielsen et al. (Science, 1991, 254, 1497-15).

In order to distinguish one barcode 500 from another, tags 530 can be added directly to the backbone 510 or to one or more branch structures 520. Some of the tags are themselves barcodes, as discussed herein. For example, a carbon nanotube can form a barcode or can be used as a tag of another type of barcode.

Barcodes 500 can be further modified by attaching another molecule 540 (for example an antibody) to one or more of the tags 530. Where bulky groups are used, modification of tag moieties 530 attached to branch sites 520 would provide lower steric hindrance for probe 550 interactions with target molecules. The tags 530 can be read by a single molecule level surface analysis method, such as SPM, as discussed herein. Different variants of imaging are known to detect morphological, topographic, chemical and/or electrical properties of tags 530, including but not limited to conductivity, tunneling current, capacitive current, etc. The specific single molecule level surface analysis method used will depend on the nature of the tag moieties 530 and the resulting signal produced. Different types of known tags 530, including but not limited to fluorescent, Raman, nanoparticle, nanotube, fullerenes and quantum dot tags 530 can be used to identify barcodes 500 by their topographical, chemical, optical and/or electrical properties. Such properties will vary as a function both of the type of tag moiety 530 used and the relative positions of the tags 530 on the backbone 510 or branch structures 520, resulting in distinguishable signals generated for each barcode 500.

In certain embodiments of the invention, illustrated in FIG. 5 and, the backbone 510 of a barcode 500, can be formed of phosphodiester bonds, peptide bonds, and/or glycosidic bonds. For example, standard phosphoramidite chemistry can be used to make backbones 510 comprising DNA chains. Other methods for making phosphodiester linked backbones 510 are known, such as polymerase chain reaction (PCR™) amplification. The ends of the backbone 510 can have different functional groups, for example, biotins, amino groups, aldehyde groups or thiol groups. The functional groups can be used to bind to probe moieties 550, or for attachment of tags 530. Tags 530 can be further modified to obtain different sizes, electrical or chemical properties to facilitate detection. For example, an antibody could be used to bind to a digoxigenin or a fluorescein tag 530. Streptavidin could be used to bind to biotin tags 530. Metal atoms can be deposited on the barcode 500 structure, for example by catalyzed reduction of a metal ion solution using an enzyme tag 530. Where the barcode 500 includes a peptide moiety, the peptide can be phosphorylated for tag 530 modification. As discussed in copending application entitled "PROGRAMMABLE MOLECULAR BARCODES," (filed Sep. 24, 2003, application Ser. No. 10/670,701) nucleotide-containing nanocodes of the invention can also be made using hybridization.

In various embodiments of the invention, barcodes include one or more tag moieties to facilitate detection and/or identification. Any detectable tag known in the art that is detectable by a single molecule level surface analysis method can be used with the barcoding of physical objects in methods of the present invention. Detectable tags can include, but are not limited to, any composition detectable by electrical, optical, spectrophotometric, photochemical, biochemical, immunochemical, or chemical techniques.

Tags can include, but are not limited to, conducting, luminescent, fluorescent, chemiluminescent, bioluminescent and phosphorescent moieties, quantum dots, nanoparticles, metal nanoparticles, gold nanoparticles, silver nanoparticles, chromogens, antibodies, antibody fragments, genetically engineered antibodies, enzymes, substrates, cofactors, inhibitors, binding proteins, magnetic particles and spin label compounds. (U.S. Pat. Nos. 3,817,837; 3,850,752; 3,939,350; 3,996,345; 4,277,437; 4,275,149; and 4,366,241.)

In aspects where the single molecule level surface analysis method is raman spectroscopy, especially SERS, Non-limiting examples of Raman tags that can be used include TRIT (tetramethyl rhodamine isothiol), NBD (7-nitrobenz-2-oxa-1,3-diazole), Texas Red dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, TET (6-carboxy-2',4,7,7'-tetrachlorofluorescein), HEX (6-carboxy-2',4,4',5',7,7'-hexachlorofluorescein), Joe (6-carboxy-4',5'-dichloro-2',7'-simethoxyflourescein) 5-carboxy-2',4',5',7'-tetrachlorofluorescein, 5-carboxyfluorescein, 5-carboxy rhodamine, Tamra (tetramethylrhodamine), 6-carboxyrhodamine, Rox (carboxy-X-rhodamine), R6G (Rhodamine 6G), phthalocyanines, azomethines, cyanines (e.g. Cy3, Cy3.5, Cy5), xanthines, succinylfluoresceins, N,N-diethyl-4-(5'-azobenzotriazolyl)-phenylamine and aminoacridine. These and other Raman tags can be obtained from commercial sources (e.g., Molecular Probes, Eugene, Oreg.).

Polycyclic aromatic compounds in general can function as Raman tags. Other tags that can be of use include cyanide, thiol, chlorine, bromine, methyl, phosphorus and sulfur. In certain embodiments, carbon nanotubes can be of use as Raman tags. The use of tags in Raman spectroscopy is known (e.g., U.S. Pat. Nos. 5,306,403 and 6,174,677).

Raman tags can be attached directly to barcodes or can be attached via various linker compounds. Nucleotides that are covalently attached to Raman tags are available from standard commercial sources (e.g., Roche Molecular Biochemicals, Indianapolis, Ind.; Promega Corp., Madison, Wis.; Ambion, Inc., Austin, Tes.; Amersham Pharmacia Biotech, Piscataway, N.J.). Raman tags that contain reactive groups designed to covalently react with other molecules, for example nucleotides or amino acids, are commercially available (e.g., Molecular Probes, Eugene, Oreg.).

Fluorescent tags that can be used in barcodes associated with physical objects include, but are not limited to, fluorescein, 5-carboxyfluorescein (FAM), 2'7'-dimethoxy-4'5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), and 5-(2'-aminoethyl)aminonaphthalene-1-sulfonic acid (EDANS). Other potential fluorescent tags are known in the art (e.g., U.S. Pat. No. 5,866,336). A wide variety of fluorescent tags can be obtained from commercial sources, such as Molecular Probes (Eugene, Oreg.). Methods of fluorescent detection of tagged molecules are also well known in the art and any such known method can be used.

Luminescent tags that can be used in barcodes associated with physical objects include, but are not limited to, rare earth metal cryptates, europium trisbipyridine diamine, a europium cryptate or chelate, Tb tribipyridine, diamine, dicyanins, La Jolla blue dye, allopycocyanin, allococyanin B, phycocyanin C, phycocyanin R, thiamine, phycoerythrocyanin, phycoerythrin R, an up-converting or down-converting phosphor, luciferin, or acridinium esters.

Nanoparticles can be used as tags are discussed herein with respect to nanocodes. Although gold or silver nanoparticles are most commonly used as tags, any type or composition of nanoparticle can be attached to a barcode and used as a tag.

The nanoparticles to be used can be random aggregates of nanoparticles (colloidal nanoparticles). Alternatively, nanoparticles can be cross-linked to produce particular aggregates of nanoparticles, such as dimers, trimers, tetramers or other aggregates. Aggregates containing a selected number of nanoparticles (dimers, trimers, etc.) can be enriched or purified by known techniques, such as ultracentrifugation in sucrose solutions.

Modified nanoparticles suitable for attachment to barcodes are commercially available, such as the Nanogold® nanoparticles from Nanoprobes, Inc. (Yaphank, N.Y.). Nanogold® nanoparticles can be obtained with either single or multiple maleimide, amine or other groups attached per nanoparticle. Such modified nanoparticles can be attached to barcodes using a variety of known linker compounds.

Tags can comprise submicrometer-sized metallic tags (e.g., Nicewamer-Pena et al., Science 294:137-141, 2001). Nicewamer-Pena et al. (2001) disclose methods of preparing multimetal microrods encoded with submicrometer stripes, comprised of different types of metal. This system allows for the production of a very large number of distinguishable tags—up to 4160 using two types of metal and as many as $8\times10^5$ with three different types of metal. Such tags can be attached to barcodes and detected. Methods of attaching metal particles, such as gold or silver, to oligonucleotides and other types of molecules are known in the art (e.g., U.S. Pat. No. 5,472,881).

Fullerenes can also be used as barcode tags. Methods of producing fullerenes are known (e.g., U.S. Pat. No. 6,358,375). Fullerenes can be derivatized and attached to other molecules by methods similar to those disclosed below for carbon nanotubes. Fullerene-tagged barcodes can be identified, for example, using various technologies.

Other types of known tags that can be attached to barcodes and detected are contemplated. Non-limiting examples of tags of potential use include quantum dots (e.g., Schoenfeld, et al., Proc. 7th Int. Conf. on Modulated Semiconductor Structures, Madrid, pp. 605-608, 1995; Zhao, et al., 1st Int. Conf. on Low Dimensional Structures and Devices, Singapore, pp. 467-471, 1995). Quantum dots and other types of tags can also be obtained from commercial sources (e.g., Quantum Dot Corp., Hayward, Calif.).

Carbon nanotubes, such as single-walled carbon nanotubes (SWNTs), can also be used as tags. Nanotubes can be detected in embodiments that employ a single molecule level surface analysis method, for example, by Raman spectroscopy (e.g., Freitag et al., Phys. Rev. B 62: R2307-R2310, 2000). The characteristics of carbon nanotubes, such as electrical or optical properties, depend at least in part on the size of the nanotube. Carbon nanotubes can be made by a variety of techniques as discussed herein.

Nucleotides or bases, for example adenine, guanine, cytosine, or thymine can be used to tag molecular barcodes other than oligonucleotides and nucleic acids. For example, peptide based molecular barcodes can be tagged with nucleotides or purine or pyrimidines bases. Other types of purines or pyrimidines or analogs thereof, such as uracil, inosine, 2,6-diaminopurine, 5-fluoro-deoxycytosine, 7 deaza-deoxyadenine or 7-deaza-deoxyguanine can also be used as tags.

Other tags include base analogs. A base is a nitrogen-containing ring structure without the sugar or the phosphate. Such tags can be detected by optical techniques, such as Raman or fluorescence spectroscopy. Use of nucleotide or nucleotide analog tags can not be appropriate where the target molecule to be detected is a nucleic acid or oligonucleotide, since the tag portion of the barcode can potentially hybridize to a different target molecule than the probe portion.

Amino acids can also be used to as tags. Amino acids of potential use as tags include but are not limited phenylalanine, tyrosine, tryptophan, histidine, arginine, cysteine, and methionine.

Bifunctional cross-linking reagents can be used for various purposes, such as attaching tags to barcodes. The bifunctional cross-linking reagents can be divided according to the specificity of their functional groups, e.g., amino, guanidino, indole, or carboxyl specific groups. Of these, reagents directed to free amino groups are popular because of their commercial availability, ease of synthesis and the mild reaction conditions under which they can be applied (U.S. Pat. Nos. 5,603,872 and 5,401,51 1). Cross-linking reagents of potential use include glutaraldehyde (GAD), bifunctional oxirane (OXR), ethylene glycol diglycidyl ether (EGDE), and carbodiimides, such as 1-ethyl-3-(3-dimethylaminopropyl) carbodiimide (EDC).

In various embodiments of the invention, the target molecules to be analyzed may be immobilized prior to, subsequent to and/or during coded probe binding. For example, target molecule immobilization may be used to facilitate separation of bound coded probes from unbound coded probes. In certain embodiments, target molecule immobilization may also be used to separate bound coded probes from the target molecules before coded probe detection and/or identification. Although the following discussion is directed towards immobilization of nucleic acids, the skilled artisan will realize that methods of immobilizing various types of biomolecules are known in the art and may be used in the claimed methods.

Nucleic acid immobilization may be used, for example, to facilitate separation of target nucleic acids from ligated coded probes and from unhybridized coded probes or coded probes hybridized to each other. In a non-limiting example, target nucleic acids may be immobilized and allowed to hybridize to coded probes, after which hybridized adjacent coded probes are ligated together. The substrate containing bound nucleic acids is extensively washed to remove unhybridized coded probes and coded probes hybridized to other coded probes. Following washing, the hybridized and ligated coded probes may be removed from the immobilized target nucleic acids by heating to about 90 to 95° C. for several minutes. The ligated coded probes may be attached to a surface and aligned by molecular combing, as disclosed above. The aligned coded probes may then be analyzed by SPM.

Immobilization of nucleic acids may be achieved by a variety of methods known in the art. In an exemplary embodiment of the invention, immobilization may be achieved by coating a substrate with streptavidin or avidin and the subsequent attachment of a biotinylated nucleic acid (Holmstrom et al., Anal. Biochem. 209:278-283, 1993). Immobilization may also occur by coating a silicon, glass or other substrate with poly-E-Lys (lysine), followed by covalent attachment of either amino- or sulfhydryl-modified nucleic acids using bifunctional crosslinking reagents (Running et al., BioTechniques 8:276-277, 1990; Newton et al., Nucleic Acids Res. 21:1155-62, 1993). Amine residues may be introduced onto a substrate through the use of aminosilane for cross-linking.

Immobilization may take place by direct covalent attachment of 5'-phosphorylated nucleic acids to chemically modified substrates (Rasmussen et al., Anal. Biochem. 198:138-142, 1991). The covalent bond between the nucleic acid and the substrate is formed by condensation with a water-soluble carbodiimide or other cross-linking reagent. This method facilitates a predominantly 5'-attachment of the nucleic acids via their 5'-phosphates. Exemplary modified substrates would include a glass slide or cover slip that has been treated in an acid bath, exposing SiOH groups on the glass (U.S. Pat. No. 5,840,862).

DNA is commonly bound to glass by first silanizing the glass substrate, then activating with carbodiimide or glutaraldehyde. Alternative procedures may use reagents such as 3-glycidoxypropyltrimethoxysilane (GOP), vinyl silane or aminopropyltrimethoxysilane (APTS) with DNA linked via amino linkers incorporated either at the 3' or 5' end of the molecule. DNA may be bound directly to membrane substrates using ultraviolet radiation. Other non-limiting examples of immobilization techniques for nucleic acids are disclosed in U.S. Pat. Nos. 5,610,287, 5,776,674 and 6,225,068. Commercially available substrates for nucleic acid binding are available, such as Covalink, Costar, Estapor, Bangs and Dynal. The skilled artisan will realize that the disclosed methods are not limited to immobilization of nucleic acids and are also of potential use, for example, to attach one or both ends of oligonucleotide coded probes to a substrate.

The type of substrate to be used for immobilization of the nucleic acid or other target molecule is not limiting. In various embodiments of the invention, the immobilization substrate may be magnetic beads, non-magnetic beads, a planar substrate or any other conformation of solid substrate comprising almost any material. Non-limiting examples of substrates that may be used include glass, silica, silicate, PDMS (poly dimethyl siloxane), silver or other metal coated substrates, nitrocellulose, nylon, activated quartz, activated glass, polyvinylidene difluoride (PVDF), polystyrene, polyacrylamide, other polymers such as poly(vinyl chloride) or poly(methyl methacrylate), and photopolymers which contain photoreactive species such as nitrenes, carbenes and ketyl radicals capable of forming covalent links with nucleic acid molecules (See U.S. Pat. Nos. 5,405,766 and 5,986,076).

Bifunctional cross-linking reagents may be of use in various embodiments of the invention. The bifunctional cross-linking reagents can be divided according to the specificity of their functional groups, e.g., amino, guanidino, indole, or carboxyl specific groups. Of these, reagents directed to free amino groups are popular because of their commercial availability, ease of synthesis and the mild reaction conditions under which they can be applied. Exemplary methods for cross-linking molecules are disclosed in U.S. Pat. Nos. 5,603,872 and 5,401,511. Cross-linking reagents include glutaraldehyde (GAD), biflinctional oxirane (OXR), ethylene glycol diglycidyl ether (EGDE), and carbodiimides, such as 1-ethyl-3-(3-dimethylaminopropyl) carbodiimide (EDC).

As indicated herein, in certain aspects of the methods of the present invention, nanocodes are detected using scanning probe microscopes (SPM). Scanning probe microscopes (SPM) are a family of instruments that are used to measure the physical properties of objects on a micrometer and/or nanometer scale. Different modalities of SPM technology are available, discussed in more detail below. Any modality of SPM analysis may be used for coded probe detection and/or identification. In general, an SPM instrument uses a very small, pointed probe in very close proximity to a surface to measure the properties of objects. In some types of SPM instruments, the probe may be mounted on a cantilever that may be a few hundred microns in length and between about 0.5 and 5.0 microns thick. Typically, the probe tip is raster-scanned across a surface in an xy pattern to map localized variations in surface properties. SPM methods of use for imaging biomolecules and/or detecting molecules of use as nanocodes are known in the art (e.g., Wang et al., Amer. Chem.Soc. Lett., 12:1697-98. 1996; Kim et al., Appl. Surface Sci. 130, 230, 340-132:602-609, 1998; Kobayashi et al., Appl. Surface Sci. 157:228-32, 2000; Hirahara et al., Phys. Rev. Lett. 85:5384-87 2000; Klein et al., Applied Phys. Lett. 78:2396-98, 2001; Huang et al, Science 291:630-33, 2001; Ando et al., Proc. Natl. Acad. Sci. USA 12468-72, 2001).

Scanning tunneling microscopy was the first SPM technique developed in the early 1980's. STM relies on the existence of quantum mechanical electron tunneling between the probe tip and sample surface. The tip is sharpened to a single atom point and is raster scanned across the surface, maintaining a probe-surface gap distance of a few angstroms without actually contacting the surface. A small electrical voltage difference (on the order of millivolts to a few volts) is applied between the probe tip and sample and the tunneling current between tip and sample is determined. As the tip scans across the surfaces, differences in the electrical and topographic properties of the sample cause variations in the amount of tunneling current. In certain embodiments of the invention, the relative height of the tip may be controlled by piezoelectric elements with feed-back control, interfaced with a computer. The computer can monitor the current intensity in real time and move the tip up or down to maintain a relatively constant current. In different embodiments, the height of the tip and/or current intensity may be processed by the computer to develop an image of the scanned surface.

Because STM measures the electrical properties of the sample as well as the sample topography, it is capable of distinguishing between different types of conductive material, such as different types of metal in a metal barcode. STM is also capable of measuring local electron density. Because the tunneling conductance is proportional to the local density of states (DOS), STM can also be used to distinguish carbon nanotubes that vary in their electronic properties depending on the diameter and length of the nanotube. STM may be used to detect and/or identify any nanocodes that differ in their electrical properties.

An STM probe tip may be scanned across a surface containing aligned coded probes to detect and identify each coded probe on the surface. Ligated coded probes may also be identified. Target molecules may be identified by determining which coded probes bind to the target molecule. In embodiments of the invention where the coded probes indicate the presence of specific sequences (such as oligonucleotide sequences), the sequence of the biomolecule may be determined from the sequence of the coded probes that bind to the target molecule.

Another modality of SPM is atomic force microscopy (AFM). Methods of biomolecule analysis by AFM are generally known in the art (e.g., Uchihashi et al., "Application of Noncontact-Mode Atomic Force Microscopy to Molecular Imaging," which recites, "Observation of organic and biological materials at molecular level has recently attracted wide attention especially in surface science involving biomolecules such as DNA. The most powerful technique that is applicable to insulating materials is atomic force microscopy (AFM). There have been several studies demonstrating the possibility of molecular-level imaging of organic molecules [Meyer et al., Nature (1991) 349:3981] and DNA [Hansma et al., Biophys J (1995) 68:1672]. However, the use of the contact or taping mode causes the local deformation of sample surfaces and the damage of thetip apex due to high loading and friction force between the tip and the sample surface. Such damage of both the tip apex and the sample surface prevent us from achieving higher-resolution imaging of molecular structures. Recent progress of AFM in the noncontact mode using the frequency modulation (FM) technique allows us to image various surfaces with true atomic resolution [Sugawara et al Science (1995) 270: 1646: Barnrnerlin et al., Probe Microscopy (1997) 1:3]. This technique can be applied to weakly adsorbed organic and biological molecules on solid surfaces without any damage of both the sample surfaces and the tip apex. In this study, we have applied noncontact-AFM to high resolution imaging of self-assembled films of nucleic acid bases adsorbed on a graphite surface and DNA adsorbed on a mica surface in an ultrahigh vacuum (UHV). The self-assembled films of the nucleic acid bases on graphite substrate were prepared by a molecular beam deposition under UHV condition and were annealed at about 330K to improve their crystallinity. The DNA was deposited on the freshly cleaved mica surface by placing a drop of DNA solution and then the sample was transferred into the UHV chamber. The noncontact-AFM measurement using Si tip was performed under the UHV at room temperature. For the self-assembled films of the nucleic acid bases, we resolved not only the lattice images of molecular packing structures but also individual molecules. Point defect and domain structures were also imaged. The images of individual molecules revealed the fine structures which depended on the molecular structures of nucleic acid bases. These noncontact-AFM images were clearly different from those obtained by STM noncontact-mode AFM for the DNA sample. As a result, we found that the removal of the water layer covering on the sample surface by annealing was reciuired for high-resolution imaging. Moreover, we resolved the right-handed helix turns in B-DNA). In AFM microscopy, the probe is attached to a spring-loaded or flexible cantilever that is in contact with the surface to be analyzed. Contact is made within the molecular force range (i.e., within the range of interaction of Van der Waal forces). Within AFM, different modes of operation are possible, including contact mode, non-contact mode and Tapping-Mode™.

In contact mode, the atomic force between probe tip and sample surface is measured by keeping the tip-sample distance constant and measuring the deflection of the cantilever, typically by reflecting a laser off the cantilever onto a position sensitive detector. Cantilever deflection results in a change in position of the reflected laser beam. As in STM, the height of the probe tip may be computer controlled using piezoelectric elements with feedback control. In some embodiments of the invention a relatively constant degree of deflection is maintained by raising or lowering the probe tip. Because the probe tip may be in actual (Van der Waal) contact with the sample, contact mode AFM tends to deform non-rigid samples. In non-contact mode, the tip is maintained between about 50 to 150 angstrom above the sample surface and the tip is oscillated. Van der Waals interactions between the tip and sample surface are reflected in changes in the phase, amplitude or frequency of tip oscillation. The resolution achieved in non-contact mode is relatively low.

In TappingMode™, the cantilever is oscillated at or near its resonant frequency using piezoelectric elements. The AFM tip periodically contacts (taps) the sample surface, at a frequency of about 50,000 to 500,000 cycles per second in air and a lower frequency in liquids. As the tip begins to contact the sample surface, the amplitude of the oscillation decreases. Changes in amplitude are used to determine topographic properties of the sample. Because AFM analysis does not depend on electrical conductance, it may be used to analyze the topological properties of non-conductive materials. Certain types of nanocodes, including but not limited to carbon nanotubes, fullerenes and nanoparticles, that differ in their topological properties may be detected and/or identified by AFM techniques.

In alternative modes of AFM, additional information may be obtained besides the topological profile of the sample. For example, in lateral force microscopy (LFM), the probe is scanned perpendicular to its length and the degree of torsion of the cantilever is determined. Cantilever torsion will be dependent on the frictional characteristics of the surface. Since the frictional characteristics of coded probes may vary depending on their composition, LFM may be useful to detect and identify different coded probes.

Another variation is chemical force microscopy (CFM), in which the probe tip is functionalized with a chemical species and scanned over a sample to detect adhesion forces between the chemical species and the sample (e.g., Frisbie et al., Science 265:2071-2074, 1994). Chemicals with differing affinities for nanocode materials, such as gold or silver, may be incorporated into an AFM probe tip and scanned across a surface to detect and identify nanocodes. Another SPM mode of potential use is force modulation imaging (Maivald et al., Nanotechnology 2:103, 1991). Uchihashi et al. ("Application of Noncontact-Mode Atomic Force Microscopy to Molecular Imaging", supra) disclose a method of biomolecule imaging using frequency modulation in non-contact mode AFM.

Other SPM modes that may potentially be used to detect and/or identify coded probes include magnetic force microscopy (MFM), high frequency MFM, magnetoresistive sensitivity mapping (MSM), electric force microscopy (EFM), scanning capacitance microscopy (SCM), scanning spreading resistance microscopy (SSRM), tunneling AFM and conductive AFM. In certain of these modalities, magnetic properties of a sample may be determined. The skilled artisan will realize that metal barcodes and other types of nanocodes may be designed that are identifiable by their magnetic as well as by electrical properties.

SPM instruments of use for coded probe detection and/or identification are commercially available (e.g. Veeco Instruments, Inc., Plainview, N.Y.; Digital Instruments, Oakland, Calif.). Alternatively, custom designed SPM instruments may be used.

In certain embodiments of the invention, a system for biomolecule analysis may comprise an information processing and control system. The embodiments are not limiting for the type of information processing system used. Such a system may be used to analyze data obtained from an SPM instrument and/or to control the movement of the SPM probe tip, the modality of SPM imaging used and the precise technique by which SPM data is obtained. An exemplary information processing system may incorporate a computer comprising a bus for communicating information and a processor for processing information. In one embodiment, the processor is selected from the Pentium® family of processors, including without limitation the Pentium® II family, the Pentium® III family and the Pentium® 4 family of processors available from Intel Corp. (Santa Clara, Calif.). In alternative embodiments of the invention, the processor may be a Celeron®, an Itanium®, an X-Scalee or a Pentium Xeon® processor (Intel Corp., Santa Clara, Calif.). In various other embodiments of the invention, the processor may be based on Intel® architecture, such as Intel® IA-32 or Intel® IA-64 architecture. Alternatively, other processors may be used.

The computer may further comprise a random access memory (RAM) or other dynamic storage device, a read only memory (ROM) or other static storage and a data storage device such as a magnetic disk or optical disc and its corresponding drive. The information processing system may also comprise other peripheral devices known in the art, such a display device (e.g., cathode ray tube or Liquid Crystal Display), an alphanumeric input device (e.g., keyboard), a cursor control device (e.g., mouse, trackball, or cursor direction keys) and a communication device (e.g., modem, network interface card, or interface device used for coupling to Ethernet, token ring, or other types of networks).

In particular embodiments of the invention, an SPM (scanning probe microscopy) unit may be connected to the information processing system. Data from the SPM may be processed by the processor and data stored in the main memory. The processor may analyze the data from the SPM to identify and/or determine the sequences of coded probes attached to a surface. By overlapping sequences of ligated coded probes, the computer may compile a sequence of a target nucleic acid. Alternatively, the computer may identify different known biomolecule species present in a sample, based on the identities of coded probes attached to the surface.

It is appreciated that a differently equipped information processing system may be used for certain implementations. Therefore, the configuration of the system may vary in different embodiments of the invention. While the processes described herein may be performed under the control of a programmed processor, in alternative embodiments of the invention, the processes may be fully or partially implemented by any programmable or hardcoded logic, such as Field Programmable Gate Arrays (FPGAs), TTL logic, or Application Specific Integrated Circuits (ASICs), for example. Additionally, the disclosed methods may be performed by any combination of programmed general purpose computer components and/or custom hardware components.

In certain embodiments of the invention, custom designed software packages may be used to analyze the data obtained from an SPM. In alternative embodiments of the invention, data analysis may be performed, using an information processing system and publicly available software packages. Non-limiting examples of available software for DNA sequence analysis include the PRISM™ DNA Sequencing Analysis Software (Applied Biosystems, Foster City, Calif.), the Sequencher™ package (Gene Codes, Ann Arbor, Mich.), and a variety of software packages available through the National Biotechnology Information Facility on the worldwide web at nbif.org/links/1.4.1. php.

In certain embodiments of the invention, solutions containing one or more barcodes can be applied to objects for security tracking purposes. Such methods are known in the art. For example, a British company (SmartWater Ltd.) has developed methods to mark valuables with fluids containing strands of digital DNA. The DNA is virtually impossible to wash off of the article and can be used to uniquely identify expensive items or heirlooms. The DNA can be detected by any forensic laboratory. Such methods can also be utilized to mark items with the molecular barcodes disclosed herein. In such applications, detection of the barcode would not require forensic analysis based on DNA sequence.

Apparatus for barcode preparation, use and/or detection can be incorporated into a larger apparatus and/or system. In certain embodiments, the apparatus can comprise a microelectro-mechanical system (MEMS). MEMS are integrated systems including mechanical elements, sensors, actuators, and electronics. All of those components can be manufactured by microfabrication techniques on a common chip, of a silicon-based or equivalent substrate (e.g., Voldman et al., *Ann. Rev. Biomed. Eng.* 1:401-425, 1999). The sensor components of MEMS can be used to measure mechanical, thermal, biological, chemical, optical and/or magnetic phenomena to detect barcodes. The electronics can process the information from the sensors and control actuator components such pumps, valves, heaters, etc. thereby controlling the function of the MEMS.

The electronic components of MEMS can be fabricated using integrated circuit (IC) processes (e.g., CMOS or Bipolar processes). They can be patterned using photolithographic and etching methods for computer chip manufacture. The micromechanical components can be fabricated using compatible "micromachining" processes that selectively etch away parts of the silicon wafer or add new structural layers to form the mechanical and/or electromechanical components.

Basic techniques in MEMS manufacture include depositing thin films of material on a substrate, applying a patterned mask on top of the films by some lithographic methods, and selectively etching the films. A thin film can be in the range of a few nanometers to 100 micrometers. Deposition techniques of use can include chemical procedures such as chemical vapor deposition (CVD), electrodeposition, epitaxy and thermal oxidation and physical procedures like physical vapor deposition (PVD) and casting. Methods for manufacture of nanoelectromechanical systems can also be used (See, e.g., Craighead, Science 290:1532-36, 2000.)

In some embodiments, apparatus and/or detectors can be connected to various fluid filled compartments, for example microfluidic channels or nanochannels. These and other components of the apparatus can be formed as a single unit, for example in the form of a chip (e.g. semiconductor chips) and/or microcapillary or microfluidic chips. Alternatively, individual components can be separately fabricated and attached together. Any materials known for use in such chips can be used in the disclosed apparatus, for example silicon, silicon dioxide, polydimethyl siloxane (PDMS), polymethylmethacrylate (PMMA), plastic, glass, quartz, etc.

Techniques for batch fabrication of chips are well known in computer chip manufacture and/or microcapillary chip manufacture. Such chips can be manufactured by any method known in the art, such as by photolithography and etching, laser ablation, injection molding, casting, molecular beam epitaxy, dip-pen nanolithography, chemical vapor deposition (CVD) fabrication, electron beam or focused ion beam technology or imprinting techniques. Non-limiting examples include conventional molding, dry etching of silicon dioxide; and electron beam lithography. Methods for manufacture of nanoelectromechanical systems can be used for certain embodiments. (See, e.g., Craighead, Science 290:1532-36, 2000.) Various forms of microfabricated chips are commercially available from, e.g., Caliper Technologies Inc. (Mountain View, Calif.) and ACLARA BioSciences Inc. (Mountain View, Calif.).

In certain embodiments, part or all of the apparatus can be selected to be transparent to electromagnetic radiation at the excitation and emission frequencies used for barcode detection by, for example, Raman spectroscopy. Suitable components can be fabricated from materials such as glass, silicon, quartz or any other optically clear material. For fluid-filled compartments that can be exposed to various analytes, for example, nucleic acids, proteins and the like, the surfaces exposed to such molecules can be modified by coating, for example to transform a surface from a hydrophobic to a hydrophilic surface and/or to decrease adsorption of molecules to a surface. Surface modification of common chip materials such as glass, silicon, quartz and/or PDMS is known (e.g., U.S. Pat. No. 6,263,286). Such modifications can include, for example, coating with commercially available capillary coatings (Supelco, Bellafonte, Pa.), silanes with various functional (e.g. polyethyleneoxide or acrylamide, etc).

In certain embodiments, such MEMS apparatus can be use to prepare molecular barcodes, to separate formed molecular barcodes from unincorporated components, to expose molecular barcodes to targets, and/or to detect molecular barcodes bound to targets.

In another embodiments, a kit is provided that includes a composition that has at least one coded probe, each coded probe including a probe molecule attached to at least one nanocode that includes a detectable non-encoding feature, the nanocode being detectable using a single molecule level surface analysis method. The probe molecule, for example, is an oligonucleotide, a polynucleotide, a nucleic acid, an antibody, an antibody fragment, a genetically engineered antibody, a single chain antibody, a humanized antibody, a protein, a receptor, a transcription factor, a peptide, a lectin, a substrate, an inhibitor, an activator, a ligand, a hormone, a cytokine, a chemokine, or a pharmaceutical.

The nanocode is, for example a carbon nanotube, a fullerene, a submicrometer metallic barcode, a nanoparticle, and a quantum dot. The non-encoding feature can be any of the non-encoding features disclosed herein, such as, for example, a start tag, a header region and/or a footer region. The nanocode can be a compressed nanocode, or a nanocode that includes reading frames.

The following examples are intended to illustrate but not limit the invention.

EXAMPLE 1

Synthesis and SPM Scanning of a Nanocode

This example illustrates the manufacture and SPM detection of a biomolecular nanocode that includes a peptide backbone and C(60) tags. A peptide was synthesized commercially using standard methods. The peptide was labeled with C(60) tags by attaching the tags to lysine residues. This was done by reacting a carboxylic group of functionalized C(60) with an amine group of lysine. The labeled polypeptide was deposited on an annealed gold SPM substrate by nano-dropping, followed by drying. The SPM was performed using a standard STM system from Digital Instruments.

Figure 3:
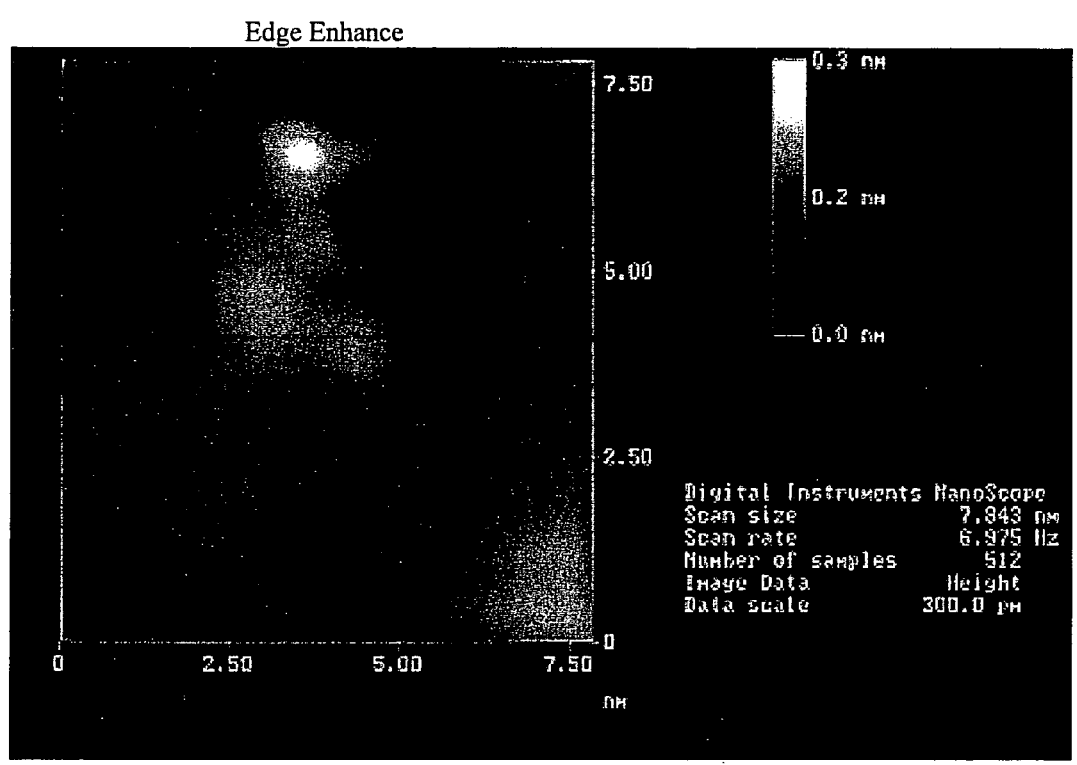
FIG. 3 is an STM image of a peptide C(60) nanocode. Multiple buckyballs were connected by a peptide. The STM scan identifies four buckyballs on graphite connected by a synthesized peptide.

FIG. 3 is an STM image of a peptide C(60) nanocode. Multiple buckeyballs were connected by a peptide. The STM scan identifies four buckeyballs on graphite connected by a synthesized peptide:

```
                                           (SEQ ID NO:1)
NH2-AAMAAKAMAAMAKAVAMAAKAVAAMAKAAA-CONH2.
```

Although the invention has been described with reference to the above example, it will be understood that modifications and variations are encompassed within the spirit and scope of the invention. Accordingly, the invention is limited only by the following claims.

---

---

What is claimed is:

1. A method comprising:
   a) providing one or more coded oligonucleotide probes, each coded oligonucleotide probe comprising an oligonucleotide attached to at least one unique nanocode wherein each nanocode comprises a feature tag;
   b) contacting at least one target nucleic acid with the one or more coded oligonucleotide probes;
   c) utilizing the feature tag to provide a quality control check for detecting nanocodes and/or distinguish target nucleotides from self-assembled coded oligonucleotide probe structures; and
   d) identifying coded oligonucleotide probes that bind to the target nucleic acid using scanning probe microscopy (SPM) to detect the nanocode and the feature tag.

2. The method of claim 1, wherein the one or more coded oligonucleotide probes comprise permutations of a linear order of nucleic acid residues, which linear order represents all possible complementary sequences for a particular length of oligonucleotide.

3. The method of claim 2, further comprising determining the nucileotide sequences of oligonucleotides that bind to the target nucleic acid.

4. The method of claim 3, further comprising determining a nucleotide sequence of the target nucleic acid from the sequences of oligonucleotides that bind to the target nucleic acid.

5. The method of claim 1, wherein the nanocode is selected from the group consisting of carbon nanotubes, fullerenes, submicrometer metallic barcodes, nanoparticles and quantum dots.

6. The method of claim 1, wherein the nucleic acid is attached to a surface.

7. The method of claim 6, further comprising ligating adjacent coded probes that are hybridized to the nucleic acid.

8. The method of claim 7, further comprising separating ligated coded probes from the target nucleic acid and non-ligated coded probes.

9. The method of claim 8, wherein the ligated coded probes form reading frames.

10. The method of claim 1, further comprising aligning the coded probes on a surface by molecular combing.

11. The method of claim 1, wherein the scanning probe microscopy is atomic force microscopy, scanning tunneling microscopy, lateral force microscopy, chemical force microscopy, force modulation imaging, magnetic force microscopy, high frequency magnetic force microscopy, magnetoresistive sensitivity mapping, electric force microscopy, scanning capacitance microscopy, scanning spreading resistance microscopy, tuiuielirig atomic force microscopy or conductive atomic force microscopy.

12. The method of claim 1, further comprising identifying the target nucleic acid from the coded probes that bind to the target nucleic acid.

13. The method of claim 1, wherein two or more target nucleic acids are present in a sample.

14. The method of claim 1, wherein at least two target nucleic acids are contacted in the sample at the same time.

15. The method of claim 1, wherein the feature tag is provided by a detectable feature tag associated with the nanocode.

16. The method of claim 15 wherein the feature tag comprises a start tag.

17. The method of claim 1, further comprising transforming the molecular nanocode to form a decompressed nanocode.

18. The method of claim 1, wherein the feature tag comprises a barcode segment.

19. The method of claim 1, wherein the feature tag comprises a header segment and an encoding segment.

* * * * *

UNITED STATES PATENT AND TRADEMARK OFFICE
CERTIFICATE OF CORRECTION

| | | |
|---|---|---|
| PATENT NO. | : 7,381,529 B2 | Page 1 of 1 |
| APPLICATION NO. | : 10/750515 | |
| DATED | : December 4, 2007 | |
| INVENTOR(S) | : Yamakawa et al. | |

It is certified that error appears in the above-identified patent and that said Letters Patent is hereby corrected as shown below:

On the Title page, in Item (56), under "Other Publications", in column 2, line 3, delete "Fingerpoints" and insert -- Fingerprints --, therefor.

In column 41, line 7, in Claim 3, delete "nucileotide" and insert -- nucleotide --, therefor.

In column 42, line 6, in Claim 11, delete "tuiuielirig" and insert -- tunneling --, therefor.

Signed and Sealed this

Twenty-sixth Day of August, 2008

JON W. DUDAS
*Director of the United States Patent and Trademark Office*

UNITED STATES PATENT AND TRADEMARK OFFICE
CERTIFICATE OF CORRECTION

PATENT NO.         : 7,381,529 B2
APPLICATION NO. : 10/750515
DATED                 : June 3, 2008
INVENTOR(S)       : Yamakawa et al.

Page 1 of 1

It is certified that error appears in the above-identified patent and that said Letters Patent is hereby corrected as shown below:

On the Title page, in Item (56), under "Other Publications", in column 2, line 3, delete "Fingerpoints" and insert -- Fingerprints --, therefor.

In column 41, line 7, in Claim 3, delete "nucileotide" and insert -- nucleotide --, therefor.

In column 42, line 6, in Claim 11, delete "tuiuielirig" and insert -- tunneling --, therefor.

This certificate supersedes the Certificate of Correction issued August 26, 2008.

Signed and Sealed this

Twenty-third Day of September, 2008

JON W. DUDAS
*Director of the United States Patent and Trademark Office*